(12) United States Patent
Menon et al.

(10) Patent No.: US 10,366,781 B1
(45) Date of Patent: Jul. 30, 2019

(54) MAPPING AND DISPLAY FOR EVIDENCE BASED PERFORMANCE ASSESSMENT

(71) Applicant: IMS Health Incorporated, Danbury, CT (US)

(72) Inventors: Piyush Menon, San Francisco, CA (US); Suresh Kannan, Foster City, CA (US); Anil Kapu, Dublin, CA (US); Elisabeth Otto, Boulder, CO (US); Amit Ranade, Fremont, CA (US)

(73) Assignee: IQVIA Inc., Parsippany, NJ (US)

(*) Notice: Subject to any disclaimer, the term of this patent is extended or adjusted under 35 U.S.C. 154(b) by 927 days.

(21) Appl. No.: 14/669,914

(22) Filed: Mar. 26, 2015

Related U.S. Application Data

(63) Continuation-in-part of application No. 14/554,553, filed on Nov. 26, 2014.

(51) Int. Cl.
*G16H 10/20* (2018.01)
*G16H 40/63* (2018.01)
*G06F 16/901* (2019.01)

(52) U.S. Cl.
CPC ......... *G16H 10/20* (2018.01); *G06F 16/9024* (2019.01); *G16H 40/63* (2018.01)

(58) Field of Classification Search
CPC .. G16H 10/20; G16H 40/63; G06F 17/30958; G06F 19/3406; G06F 19/363
See application file for complete search history.

(56) References Cited

U.S. PATENT DOCUMENTS

| 6,574,621 | B1 | 6/2003 | Lautzenheiser |
| 6,871,783 | B2 | 3/2005 | Kaafarani |
| 8,301,464 | B1 | 10/2012 | Cave |
| 2003/0167187 | A1 | 9/2003 | Bua |
| 2006/0161456 | A1 | 7/2006 | Baker |
| 2006/0253773 | A1 | 11/2006 | Hsieh |
| 2011/0112416 | A1 | 5/2011 | Myr |
| 2011/0119072 | A1 | 5/2011 | Lipner |

(Continued)

OTHER PUBLICATIONS

Otto, "SiteOptimizer Demo and Roadmap," presented at a SCOPE conference, Feb. 2014, 18 pages.

*Primary Examiner* — Victoria P Augustine
*Assistant Examiner* — Chad A Newton
(74) *Attorney, Agent, or Firm* — Fish & Richardson P.C.

(57) ABSTRACT

A computer-implemented method for providing a user with a performance indicator score includes receiving a first transaction message that includes historical clinical-trial performance data from one or more processors at a clinical research organization and receiving a second transaction message with health records data with parameters indicative of insurance claims data. The received historical clinical-trial performance data and the prescription data is translated into an updated database. Related records within the updated database are identified and one or more key performance indicators included in the data at the updated database for a first physician are identified. A score for each of the one or more key performance indicators are calculated and a performance indicator score record for the first physician is generated based on the calculated scores for each of the one or more key performance indicators. A multi-dimensional chart for organizing and evaluating investigators is generated.

20 Claims, 16 Drawing Sheets

(56) References Cited

U.S. PATENT DOCUMENTS

| | | | |
|---|---|---|---|
| 2012/0232949 A1* | 9/2012 | Lingard | G06Q 10/04 705/7.28 |
| 2013/0110771 A1 | 5/2013 | Merriman | |
| 2014/0236668 A1* | 8/2014 | Young | G06Q 10/10 705/7.28 |
| 2016/0147953 A1 | 5/2016 | Menon et al. | |

* cited by examiner

FIG. 3

MAPPING AND DISPLAY FOR EVIDENCE BASED PERFORMANCE ASSESSMENT

CROSS-REFERENCE TO RELATED APPLICATIONS

This application is a continuation-in-part application of and claims priority to U.S. application Ser. No. 14/554,553, filed on Nov. 26, 2014, the entire contents of which is incorporated herein by reference.

BACKGROUND

The determination of the most efficient candidates to participate in a clinical trial can be one of the most important factors for clinical trial organizations. The assessment of investigators, that is, physicians or doctors that participate in clinical trials, is therefore essential.

SUMMARY

In one general aspect, a computer-implemented method for providing a user with a performance indicator score includes receiving a first transaction message that includes historical clinical-trial performance data from one or more processors at a clinical research organization and receiving a second transaction message with health records data with parameters indicative of insurance claims data. The received historical clinical trial performance data and the health records data is translated into an updated database. Related records within the updated database are identified and one or more key performance indicators included in the data at the updated database for a first physician are identified. A score for each of the one or more key performance indicators are calculated and a performance indicator score record for the first physician is generated based on the calculated scores for each of the one or more key performance indicators.

This and other implementations can each optionally include one or more of the following features. In another aspect, receiving a second transaction message with health records data includes receiving patient data and prescriber data. In yet another aspect generating, based on the calculated scores for each of the one or more key performance indicators, a performance indicator score record for the first physician includes calculating a weighted average of the calculated scores for each of the one or more key performance indicators. In another aspect, the weight of particular key performance indicator to the performance indicator score is based on a therapeutic area.

In another aspect, generating, based on the calculated scores for each of the one or more key performance indicators, a performance indicator score record for the first physician includes calculating a performance indicator score based on an algorithm. In another aspect, the performance indicator score for the first physician is presented to the user. In yet another aspect, a performance indicator score record for the first physician includes generating a performance indicator score record based on a subset of the one or more key performance indicators.

In another aspect, the subset of the one or more key performance indicators used to calculate the performance indicator score record for the first physician is selected by the user. In yet another aspect, one or more key performance indicators for a second physician are identified and a score for each of the one or more key performance indicators are calculated. A performance indicator score record for the second physician is generated based on the calculated scores for each of the one or more key performance indicators.

In another aspect, the first physician and second physician are ranked by the associated performance indicator score and the ranked list is presented to the user. In another aspect, the ranked list is presented to the user based on the score for a particular key performance indicator. In yet another implementation, receiving a first transaction message that includes historical clinical-trial performance data from one or more processors at a clinical-research organization includes receiving a data file, a stream of data or a datagram.

In a second general aspect, a computer-implemented method for organizing clinical trial data includes obtaining identities of a plurality of investigators and data representing a set of attributes associated with each of the plurality of investigators from a first data set and a second data set, where the first data set containing proprietary data associated with at least one of the investigators, and the second data set containing third-party data associated with at least one of the investigators. Receiving a user input indicating a subset of attributes from the set of attributes associated with each of the plurality of investigators. Generating a multi-dimensional chart that organizes the identities of the plurality of investigators based on the subset of attributes and a user designation of selected dimensions to reflect two or more of attributes from the subset of attributes. The multi-dimensional chart includes a first dimension representing a first attribute from the subset of attributes, a second dimension representing a second attribute from the subset of attributes, and a plurality of icons. Each icon represents an identity of one of the plurality of investigators, and each icon is positioned on the multi-dimensional chart along the first dimension according to a value of the first attribute associated with the represented identity and along the second dimension according to a value of the second attribute of the represented identity. A graphical property of each icon represents a value of a third attribute of the represented identity. Linking each of the plurality of icons to a selectable record in the database so that user interactions with ones of the plurality of icons cause one or more attributes associated with the ones of the plurality of icons to be altered within the database. Providing a graphical user interface (GUI) including the multi-dimensional chart and a clinical trial roster for display on a computing device. Receiving a user selection of one or more icons from the multi-dimensional chart for inclusion in a clinical trial, and in response to the user selection, adding identities of investigators represented by the one or more selected icons to the clinical trial roster. And, storing the identities of investigators represented by the one or more selected icons in association with the clinical trial roster and the multi-dimensional chart.

This and other implementations can each optionally include one or more of the following features. In another aspect, the method includes modifying an attribute associated with at least one of the added identities in response to adding the identities of investigators represented by the one or more selected icons to the clinical trial roster, and causing a linked icon in another multi-dimensional chart to be modified based on the attribute associated with the at least one of the added identities being modified. In yet another aspect, the method includes selecting a subset of identities of the plurality of investigators, the subset of identities including only identities of investigators for whom data is available in both the first and second data sets. In addition, generating the multi-dimensional chart includes generating the multi-dimensional chart to organize the identities in the subset of identities of the plurality of investigators, where each icon of the plurality of icons represents an identity from the subset of identities of the plurality of investigators. In another aspect, the method includes receiving an approval indication for the clinical trial roster, and storing the identities of investigators represented by the one or more selected icons in association with the clinical trial roster and the multi-dimensional chart is performed in response to receiving the approval indication.

In another aspect, the user input indicating a subset of attributes includes the user designation, where the user designation indicates to represent the first attribute by the first dimension of the multi-dimensional chart and the second attribute by the second dimension of the multi-dimensional chart. In yet another aspect, the subset of attributes includes the third attribute, and the user input indicating a subset of attributes includes the user designation, where the user designation indicates to represent the first attribute by the first dimension of the multi-dimensional chart, the second attribute by the second dimension of the multi-dimensional chart, and the third attribute by the graphical property of each icon of the multi-dimensional chart.

In another aspect, the data representing the set of attributes associated with each of the plurality of investigators includes raw data and performance indicator scores. In yet another aspect, a color of each icon represents a fourth attribute of the represented investigator. In another aspect, the method includes altering icons associated with the identities of investigators that have been added to the clinical trial roster. In another aspect, the method includes providing a list of attributes associated with an identity of an investigator when a user selection device hovers over an icon that represents the identity of the investigator for display.

In another aspect, the method includes receiving a user input assigning an investigator included in the clinical trial roster to an investigation site, and storing the assigned investigation site in association with the investigator's identity in the clinical trial roster. In another aspect, the method includes receiving an approval indication for the clinical trial roster, and sending notifications to investigators included in the clinical trial roster in response to receiving the approval indication, where the notifications indicate that each investigator has been selected to participate in the clinical trial. Each notification can include information related to a site to which the investigator has been assigned for performing the clinical trial. Each notification can include a target number of patients for the clinical trial.

In another aspect, the method includes selecting a first subset of identities from among the plurality of investigators based on a first filtering criteria. Generating the multi-dimensional chart includes generating the multi-dimensional chart to organize identities in the first subset of identities of the plurality of investigators, where each icon of the plurality of icons represents an identity from the first subset of identities of the plurality of investigators. In addition, the method can include selecting a second subset of identities from among the first subset of identities, based on a second filtering criteria; and refining the multi-dimensional chart to organize identities in the second subset of identities, wherein each icon of the plurality of icons represents an identity from the second subset of identities. The first filtering criteria can be an investigator attribute from one of the first or second data set, and the second filtering criteria can be an investigator attribute from the other of the first or second data set.

In another aspect, the clinical trial roster can be a first clinical trial roster, and the method can include receiving a second clinical trial roster, where the second clinical trial roster is a prior generated roster, and where generating the multi-dimensional chart includes generating the multi-dimensional chart to organize identities from the second clinical trial roster, with each icon of the plurality of icons representing an identity from the second clinical trial roster.

Other implementations of the above aspects include corresponding systems, apparatus, and computer programs, configured to perform the actions of the methods, encoded on computer storage devices. The details of one or more implementations of the subject matter described in this specification are set forth in the accompanying drawings and the description below. Other features, aspects, and advantages of the subject matter will become apparent from the description, the drawings, and the claims.

DESCRIPTION OF DRAWINGS

FIGS. 2-9 illustrate example user interfaces of user interaction with a webpage application of a performance indicator tool.

DETAILED DESCRIPTION

This disclosure generally describes computer-implemented methods, software, and systems for determining a performance indicator score that reflects the assessment of the performance of an investigator within clinical trials. The performance indicator score for a particular investigator, or physician, may be determined based on one or more key performance indicators (KPIs). The computer-implemented methods, systems and software integrate the historical clinical trial performance data source and the IMS data source to determine the best performing investigators. The data is visualized through the performance assessment application in the form of maps, tables, charts, and investigator scorecards. In some implementations, the data is visualized in user interactive multi-dimensional charts, and clinical trial rosters can be created and evaluated through user interaction with the charts.

Clinical trials are used to determine whether a new biomedical or behavioral interventions are safe, efficacious, and effective. Clinical trials may involve research studies on human subjects and are typically performed by health care providers or physicians that treat patients. The health care provider or physician may ask the patient or clinical trial subject to answer specific questions about a particular pharmaceutical product, vaccine, dietary supplements, or treatment regime. It is important that physicians participating in clinical trials are effective, and gather the required data from patients within the desired time period. It is also important that clinical trial organizations have the ability to access a quantifiable assessment of physicians. Having access to the quantifiable assessment scores of physicians make staffing a clinical trial a more reliable process.

Typically, a large percentage of all clinical trials under-enroll patients and in some instances, not even a single patient is screened. Contracting and monitoring unproductive clinical trial sites leads to a waste in time and revenue. Clinical trial organizations need to identify and enroll proven clinical trial performers, and productive sites that have access to screen a large number of patients. This will help to avoid the enrolling chronically underperforming physicians and sites into clinical trials. Identifying proven performers can also lead to enrolling physicians with experience in specialties that align with a particular clinical trial, obtaining results in a timely manner, and enrolling sites that have access to a large population of patients. In addition, some implementations may enable more efficient use and organization of investigator data, thereby, reducing computing resources required to both maintain and process investigator data, and to coordinate logistics related to organizing investigators for clinical trials.

Figure 1:
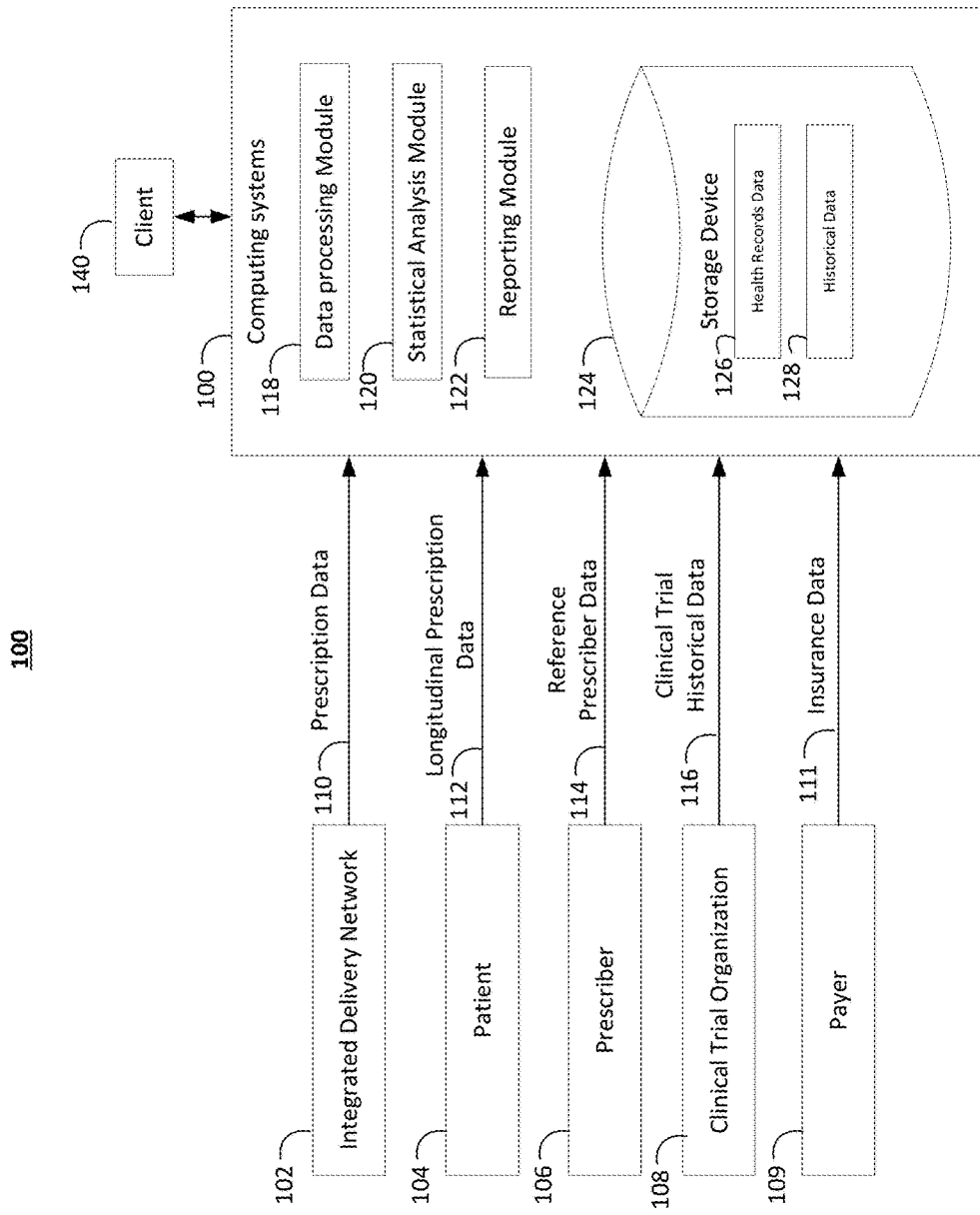
FIG. 1 illustrates an example of an analytical infrastructure system implemented in a computing system 100.

FIG. 1 illustrates an example analytical infrastructure system implemented in a computing system 100. The computing system may be implemented as a data processing apparatus that is capable of providing the functionality discussed herein, and may include any appropriate combination of processors, memory, and other hardware and software that can receive appropriate medical data and process the data as discussed below. At a high-level, the illustrated example computing system 100 receives various data from sources that are participants in the healthcare system. The sources may include integrated delivery networks (IDNs) 102, patient system 104, prescriber system 106, clinical trial organization 108, and payer system 109. The data may include consumption data 110, longitudinal patient data 112, reference prescriber data 114, clinical trial historical data 116, and payers insurance data 111.

FIG. 1 illustrates the process by which an analytical infrastructure is able to integrate historical data received from clinical trial organizations and IMS health data that includes insurance claims data, patient data and prescriber data. The data sources may be combined to form a universal data set that integrates the data sources. The integrated data sources may be stored as an updated database. The updated database may be an extension to the one or more databases that store the health records data and/or the clinical trial data. The updated database may be a computational database. The updated database may have the processing capability to execute extensive computations and calculations. The updated database may perform extensive calculations and computations on the health records data and the clinical trial historical data sources at the updated database high processing speeds. The updated database may be an energy efficient and time efficient database. The updated database may process large amounts of clinical trial historical data and health records data at very high speeds. The updated database may have the processing ability to allow the calculations and computations carried out on the data sources at the updated database to be quick and effective.

It is important to understand that the system may be configured to preserve patient privacy, and will not store nominative data in an aggregated database but only de-identified data.

The physician prescription data 110 may include data regarding prescriptions prescribed by physicians within an IDN. The prescription data 110 may be received directly from one or more IDNs 102 and represent data reflecting all prescriptions for pharmaceutical products issued by physicians within the one or more IDNs 102, including information about the type of prescription used to obtain the product and the payment method used to purchase the product. As noted previously, this information may be sanitized and aggregated to protect patient privacy. The prescription data may include the total revenue spent on prescriptions based on the specific drug. In some implementations, the data may be based on the total revenue spent on a specific drug in a specific geographic location. Though FIG. 1 shows the prescription data 110 being provided directly from the one or more IDNs 102 to the computing system 100, the prescription data 110 may be collected by one or more other intermediate systems and then provided to the computing system 100.

The longitudinal patient data 112 may include sanitized retail patient-level data for the one or more patient systems 104. For example, the longitudinal patient data 112 may include information about retail pharmacy-sourced prescription insurance claims, retail pharmaceutical scripts, patient electronic medical records, and/or patient profile data. Longitudinal patient data 112 includes information about aspects of care for the one or more patient systems 104. Though FIG. 1 illustrates the longitudinal patient data 112 as being received by the computing system 100 directly from one or more patient systems 104, the longitudinal patient data 112 may be collected by one or more other systems and then provided to the computing system 100 in a manner analogous to the similar approach discussed for prescription data 110. Moreover, the longitudinal patient data 112 may not originate from the one or more patient systems 104, but may rather be provided by one or more prescribers/physicians with whom the patient interacts, insurance companies to which a patient submits insurance claims, and/or retailers at which a patient purchases a pharmaceutical product. In some implementations, the longitudinal patient data 112 may originate from one or more pharmaceutical companies.

The reference prescriber data 114 may include detailed data about health care providers and physicians. The reference prescriber data may include details such as the specialty of a physician, the IDN affiliation of a physician, and/or the health insurance network that the physician may be associated with. This data may be obtained through prescriptions written by the particular prescribing physician. Though FIG. 1 illustrates the reference prescriber data 114 as being received by the computing system 100 directly from one or more prescriber systems 106, the reference prescriber data 114 may be collected by one or more other systems and then provided to the computing system 100 in a manner analogous to the similar approach discussed for retail consumption data 110. Moreover, the reference prescriber data 114 may not originate from the one or more prescriber systems 106, but rather be created and/or maintained by one or more other entities (e.g., government agencies or professional medical organizations) that track information about the prescribing behavior of prescribers 106.

The clinical trial historical data 116 may include information about clinical trial that were conducted by clinical trial organizations in the past. The clinical trial historical data may include the sites and the physicians that participated in clinical trials in the past. The clinical trial historical data may include the date of past trials, and the run period of the trial. For each physician that participated in the trial, the historical data may include the number of patients screened by the physician, the length of time the physician took to enter the data collected. The clinical trial historical data may include any other data that was collected during clinical trials in the past. Though FIG. 1 illustrates the clinical trial historical data 116 as being received by the computing system 100 directly from clinical trial organization 108, the clinical trial data 116 may be collected by one or more other systems and then provided to the computing system 100 in a manner analogous to the similar approach discussed above.

The insurance data 111 may include information about insurance companies covering the cost of prescriptions. For example, the insurance data 111 may include information about how much of a prescription's cost was covered by the insurance company or by Medicaid. Though FIG. 1 illustrates the insurance data 111 as being received by the computing system 100 directly from one or more payer system 109, the insurance data 111 may be collected by one or more other systems and then provided to the computing system 100.

The various types of data just discussed, which may include prescription data 110, longitudinal prescription data 112, reference prescriber data 114, clinical trial historical data 116, and insurance data 111, are received by computing system 100 in order to derive conclusions based on the data. As noted previously, by the time the data is received by computing system 100, it should have been sanitized so that the data does not include private or confidential information that computing system 100 should not able to access.

For illustrative purposes, computing system 100 will be described as including a data processing module 118, a statistical analysis module 120, a reporting module 122, and a storage device 124. However, the computing system 100 may be any computing platform capable of performing the described functions. The computing system 100 may include one or more servers that may include hardware, software, or a combination of both for performing the described functions. Moreover, the data processing module 118, the statistical analysis module 120, and the reporting module 122 may be implemented together or separately in hardware and/or software. Though the data processing module 118, the statistical analysis module 120, and the reporting module 122 will be described as each carrying out certain functionality, the described functionality of each of these modules may be performed by one or more other modules in conjunction with or in place of the described module.

The data processing module 118 receives and processes one or more of prescription data 110, longitudinal patient data 112, reference prescriber data 114, clinical trial historical data 116, and insurance data 111. In processing the received data, the data processing module 118 may filter and/or mine the prescription data 110, longitudinal patient data 112, clinical trial historical data 114, pharmaceutical purchase data 116, and insurance data for specific information. The data processing module 118 may filter and/or mine the received prescription data 110, longitudinal patient data 112, reference prescriber data 114, clinical trial historical data 116, and insurance data 111 for specific pharmaceuticals. After processing the received prescription data 110, longitudinal patient data 112, reference prescriber data 114, clinical trial historical data 116, and insurance data 111, the data processing module 118 aggregates the processed data into patient data 126 and prescriber data 128. These groups of data may be stored in storage device 124.

In other implementations, the data processing module 118 may simply sort and store, in storage device 124, processed prescription data 110, longitudinal patient data 112, reference prescriber data 114, clinical trial historical data 116 and insurance data, the data processing module 118 for later use by other modules.

The computing systems integrate the sources of data received. The reporting module 122 prepares reports based on the integrated data sources at the computing system 100. The reports prepared by the reporting module 122 may include the performance indicator score for a particular physician. The performance indicator score may be a weighted average of score for one or more key performance indicators associated with the physician.

Additionally, in some implementations, the reports generated may be either dynamic or static. The reporting module 122 may generate a report that includes data presented in one or more static formats (e.g., a chart, a graph, or a table) without providing any mechanism for altering the format and/or manipulating the data presented in the report. In such an implementation, the data presentation is generated and saved without incorporating functionality to update the data presentation. In some implementations, the reporting module 122 provides a static report in a PDF, spreadsheet, or XML format. Such a format generally provides an understanding of the reporting module 122 as textual data or a visualization, but other forms of presenting conclusions such as audio, video, or an animation are not excluded as potential results from reporting module 122. The reporting module 122 may provide a static report in a PowerPoint format.

Additionally or alternatively, the reporting module 122 may generate a report that includes controls allowing a user to alter and/or manipulate the report itself interactively. For example, the reporting system may provide a dynamic report in the form of an HTML document that itself includes controls for filtering, manipulating, and/or ordering the data displayed in the report. Moreover, a dynamic report may include the capability of switching between numerous visual representations of the information included in the dynamic report. In some implementations, a dynamic report may provide direct access as selected by a user to some or all of the patient data 126 and prescriber data 128 prepared by the data processing module 118 and/or the statistical analysis module 120, as opposed to allowing access to only data and/or ratings included in the report itself. In some implementations, data displayed in a dynamic report may be linked to the underlying database records stored at computing system 100 such that user interaction with the report causes modifications to associated database records.

One or more clients 140 may interface with the computing system 100 to request and receive reports created by the reporting system. In some implementations, the one or more clients 140 may include a web browser that provides Internet-based access to the computing system 100. Through the web browser, a user of a client 140 (e.g., a clinical trial manager, a wholesaler, a retail outlet, or a prescriber) may request a static or dynamic report from the reporting system as discussed above.

There may be any number of clients 140 associated with, or external to, the example computing system 100. While the illustrated example computing system 100 is shown in communication with one client 140, alternative implementations of the example computing system 100 may communicate with any number of clients 140 suitable to the purposes of the example computing system 100. Further, the term "client" and "user" may be used interchangeably as appropriate without departing from the scope of this disclosure. Moreover, while the client 140 is described in terms of being used by a single user, this disclosure contemplates that many users may share the use of one computer, or that one user may use multiple computers.

The illustrated client 140 is intended to encompass computing devices such as a desktop computer, laptop/notebook computer, wireless data port, smartphone, personal digital assistant (PDA), tablet computing device, one or more processors within these devices, or any other suitable processing device. For example, the client 140 may include a computer that includes an input device, such as a keypad, touch screen, or other device that can accept user information, and an output device that conveys information associated with the operation of the computing system 100. The input device may be used by client 140 to provide instructions to computing system 100 that computing system 100 can execute to provide information requested by client 140 from the various data that computing system 100 receives. The analytical infrastructure may be supported on a webpage application that a client may use to view the data received by the computing system at the analytical infrastructure.

Figure 2:
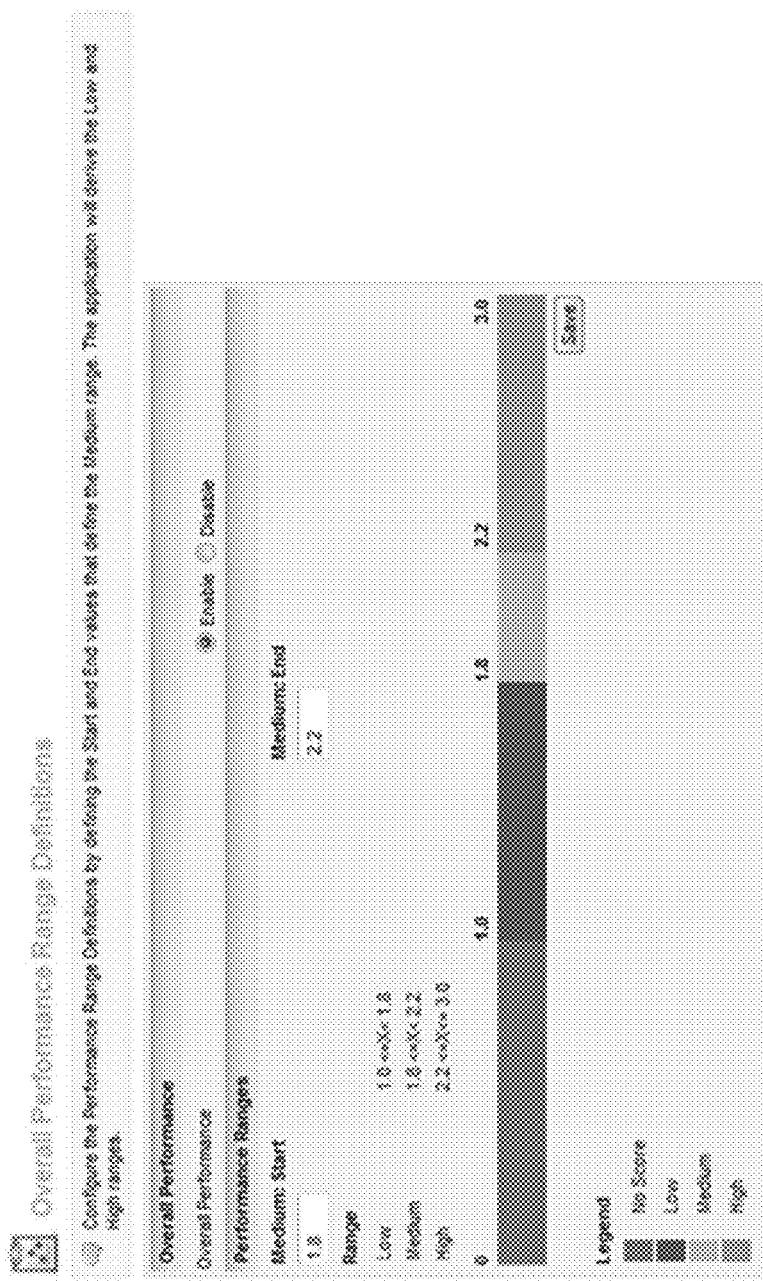
Figure 4:
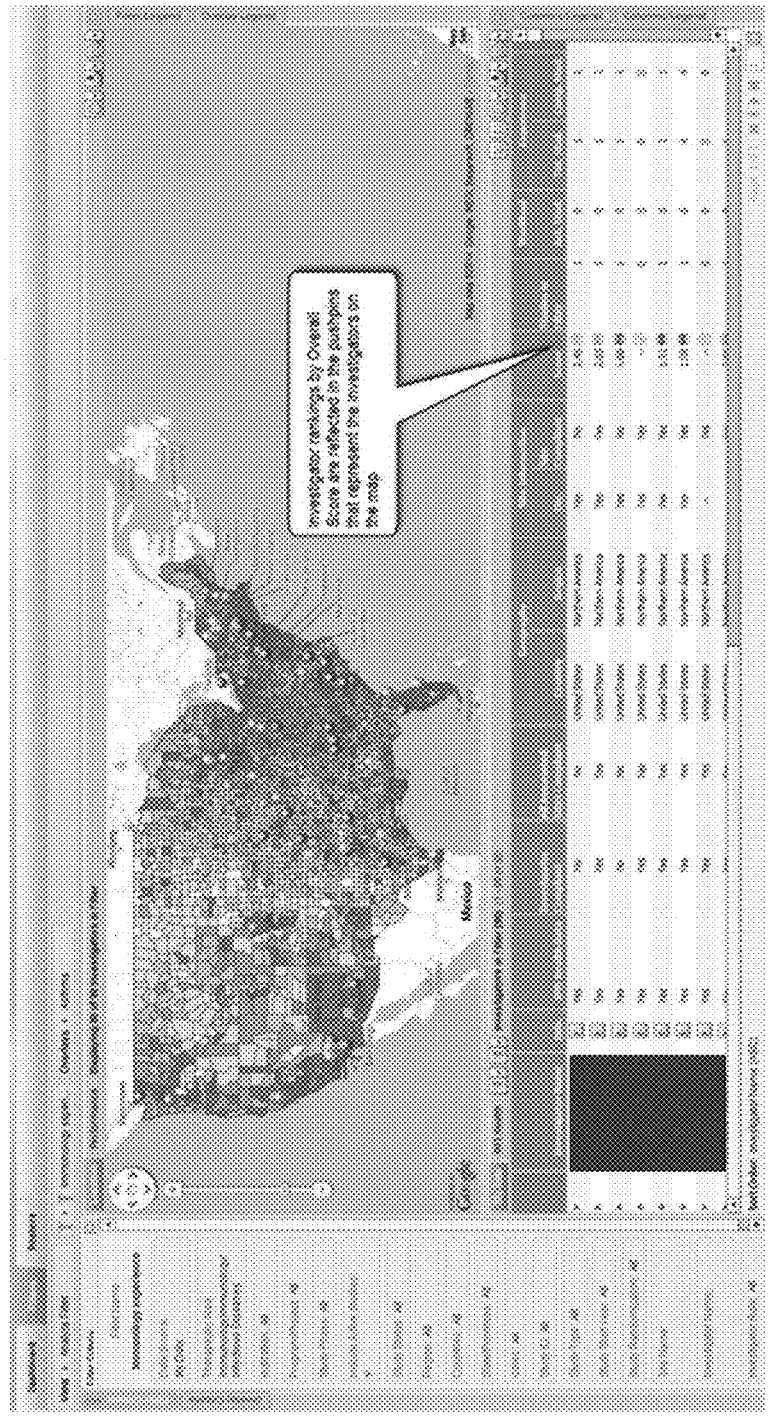

FIG. 2 illustrates an example administrative user interface for user interaction with an application of a performance indicator offering. In some implementations, interface 200 may be displayed to an internal user at IMS. The internal IMS user may act as an administrative user for the performance indicator offering. The administrative user may configure the performance indicator score range definitions. The administrative user may define the start and end values that define the medium range of the performance indicator score. The computing systems at the analytical infrastructure may then determine the low and high ranges for the performance indicator score based on the input values from the administrative user. In some implementations, the administrative user may define the values for the low, medium, and high performance indicator scores. The administrative user may define the values for the range of indicator score by any suitable means. The performance scores displayed to the end user, based on the data set of the filters selected by the user, as illustrated in FIG. 4, may be based on the performance indicator score range defined by the administrative user. For the example illustrated in FIG. 2, the administrative user may set the start value for the medium performance indicator score at 1.8 on a scale of 1 to 3, and may set the end value for the medium performance indicator score at 2.2. In some implementations, the end user may have the ability to define the performance indicator range. The performance indicator score may be based on a scale of 1 to 10, 1 to 100, or any other suitable scale.

Figure 3:
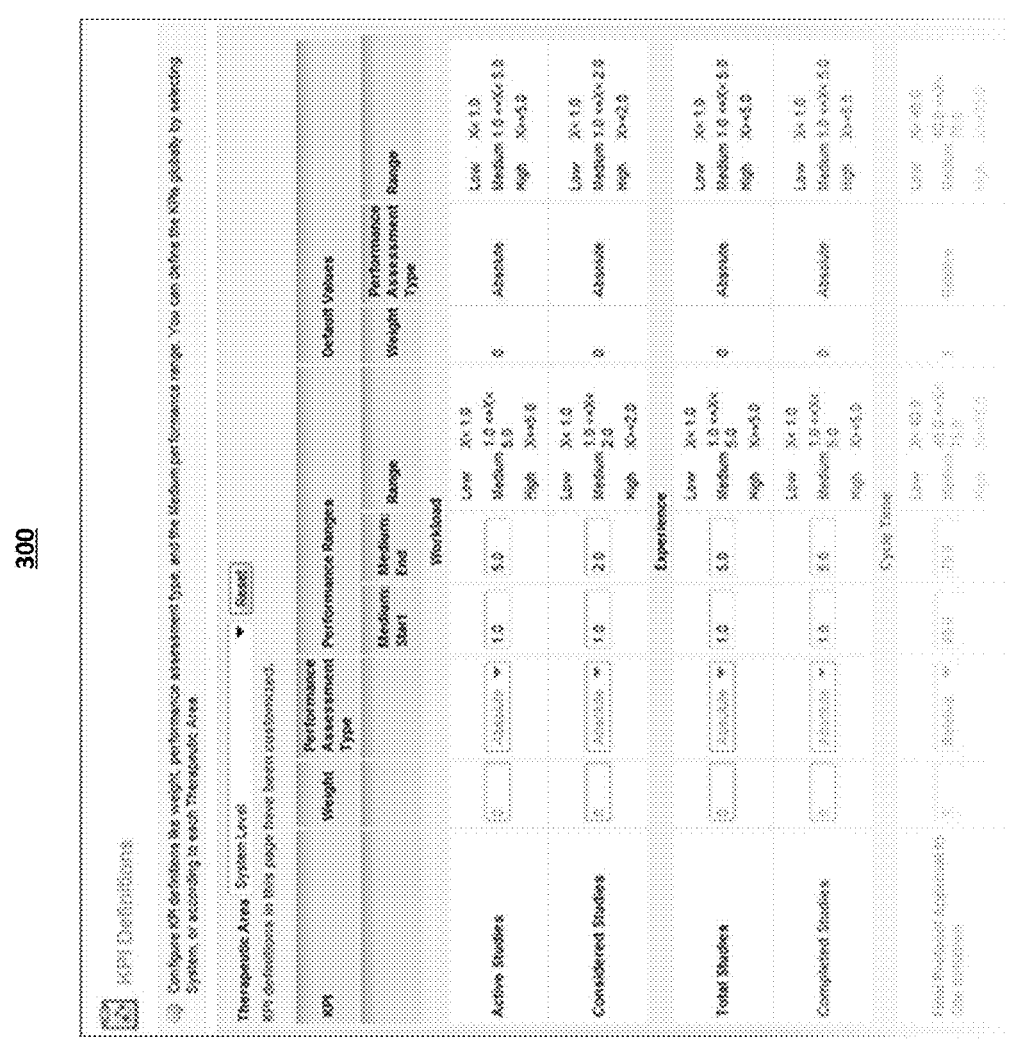

FIG. 3 illustrates an example administrative user interface for the performance indicator offering. As described above, an administrative user may be an internal user at IMS. Interface 300 may be displayed when the administrative user logs into a secure connection to the performance indicator offering. The administrative user may define the key performance indicators to determine how each key performance indicator contributes to the overall performance indicator score. The determination set by the administrator may be used across the one or more clinical trial organizations and/or pharmaceutical companies that utilize the performance indicator offering to evaluate investigators to staff on a clinical trial. In some implementations, the end user at the clinical trial organization and/or pharmaceutical company may have the ability to configure the contribution of each key performance indicator to the overall performance indicator score for an investigator. The end user at the clinical trial organization and/or pharmaceutical company may have the ability to identify which key performance indicators should be included to determine the overall performance indicator score for an investigator.

As illustrated in FIG. 3, the user may define the key performance indicators across the entire system by selecting the system level option from a drop down tab. The user may also define the key performance indicators according to a specific therapeutic area by selecting the therapeutic area from the therapeutic area drop down tab. The user interface may list the key performance indicators, the performance range associated with each key performance indicator, and the default value associated with each key performance indicator. The list of key performance indicators may include active studies, considered studies, total studies, completed studies, final protocol approval to site initiation, institutional review board approval to site initiation, site initiation to first patient screened, site initiation to last patient screened, site initiation to last patient randomized, patients randomized, percent of target randomized, screening rate, screen failure percent, randomization rate, dropout percent, data entry lag, time to resolve queries, protocol violations, regulatory audits, and queries. The key performance indicators may further include in other suitable key performance indicator that may be revealed from the data at analytical infrastructure. In some implementations, the administrative user may define the parameters for a key performance indictor based on the data set available at the analytical infrastructure. The key performance indicators may be grouped into one or more categories. The categories may include Experience, Workload, Cycle Time, Throughput, Data management, and Data Quality. The one or more key performance indicators may be grouped into any suitable category.

The Workload and Experience categories may include the active studies, considered studies, total studies and completed studies key performance indicators. These categories of key performance indicators measure the experience of investigators in terms of the number of clinical trial studies an investigator has participated in the past. The investigator experience may be gathered from the clinical trial historical data that is received by the computing systems at the analytical infrastructure. The active studies indicator identifies the number of currently active clinical trial studies that an investigator is currently participating. The data processing module at the analytical infrastructure may field and/or mine the clinical trial historical data received. The data processing module may include a study as an active study when evaluating the performance of an investigator based on administrative set criteria. The administrative user may exclude active and historical clinical trial studies data from the evaluation of the performance indicator score of an investigator. The performance data from the sites for any excluded clinical trial studies may not be included in the performance analysis. In some implementations, the end user may have the ability to determine whether data from an active clinical trial study should be included in the evaluation of the performance indicator score of an investigator.

The considered studies indicator identifies the number of unique clinical trial studies for which an investigator is being considered to participate. The data processing module may include a clinical trial study when evaluating the performance of an investigator when the investigator is included on a roster for a clinical trial study. The total studies indicator identifies the total number of clinical trial studies that an investigator has participated. In some implementations, this indicator may include clinical trials that have already been completed and clinical trials that are currently active. The completed studies indicator identifies the number of studies that an investigator has completed work.

The Cycle time category may include final protocol approval to site initiation, institutional review board approval to site initiation, site initiation to first patient screened, site initiation to last patient screened, and site initiation to last patient randomized key performance indicators. The cycle time category of key performance indicators measures how quickly an investigator was able to achieve site initiation and patient screening milestones. The final protocol approved to site initiation indicator measures the time between the date the final protocol was approved and the date the site initiated the study. The institutional review board approval to site initiation indicator measures the time between the date of the country level institutional review board approval for a clinical trial and the date the site initiated the clinical trial. The site initiation to first patient screened indicator measures the time between the site's initiation date and the date when the first patient was screened for a clinical trial study. The site initiation to last patient screen measures the time between the site's initiation date and the date when the last patient was screened at the site. The site initiation to last patient randomized indicator measures the time between the site's initiation date and the date when the last patient was randomized into the site. The time period for the key performance indicators that fall within the cycle time category may measure time in days, weeks, quarters, or months, or any other suitable time period. In some implementations, the administrative user may set the time unit used.

The Throughput category may include patients randomized, percent of target randomized, screening rate, screen failure percent, randomization rate, and dropout percent key performance indicators. The throughput category of key performance indicators are used to evaluate an investigator's ability to process numbers of patients. The patients randomized indicator may be used to show the patient volume by calculating the number of patients who were randomized by an investigator. The percent of target randomized indicator may indicate the investigator's ability to meet commitments by calculating the patients who were randomized as a percentage of the original target. The screening rate indicator may show an investigator's patient volume by calculating the average number of patients who were screened per site per unit time. The screen failure percentage may measure an investigator's ability to screen patients by calculating the average percentage of patients who failed screening out of the total number of patients screened. The randomization rate indicator shows an investigator's patient volume by calculating the average number of patients who were randomized per site, per unit time. The dropout percent shows an investigator's ability to retain patients by calculating the average percentage of patients who left a clinical trial study after being randomized.

The Data Management and Quality category of key performance indicators may include data entry lag, time to resolve queries, protocol violations, regulatory audits, and queries indicators. The data entry lag indicator may evaluate the average time between a patient visit and a data entry for the visit. The time to resolve queries indicator may measure the average time between the query and the resolution. The protocol violations indicator may measure an investigator's ability to follow the protocol for a clinical trial without incurring violations. The regulatory audits indicator may evaluate how frequently the investigator generated regulatory audits. The queries indicator may evaluate how frequently the investigator generated queries.

For each listed key performance indicator, the administrative user has the ability to configure the medium start and medium end ranges. In some implementations, the administrative user may configure the application to run using the default values. In some implementations, the end user may have the ability to configure the performance ranges for one or more of the key performance indicators.

FIG. 4 illustrates an example user interface for user interaction with an application of a performance indicator offering. The end user may be a client 140 that accesses the web-application to the computing systems 100 at the analytical infrastructure. The user may be a user at a clinical trial organization, or the user may be a representative at a pharmaceutical company that is interested in staffing a clinical trial. The end user may use the performance indicator offering to identify a list of investigators, or physicians, that are ranked based on their clinical trial performance. The end user may use the performance indicator offering to compare one or more physicians based on one or more sets of metrics. The performance indicator offering may compare the one or more physicians based on patient availability derived from health insurance claim information. Interface 400 may be displayed when a user logs into a secure connection with the performance indicator offering. The user may log into the application by providing a user specific user name and password, or any other suitable user authentication mechanism. The webpage may be specific to individual users of the application, that is, the webpage generated is specific to the user. In some implementations, the user may have the option to customize the information displayed on the web page. The performance indicator offering may enable the user to evaluate the performance of an investigator against other investigators on a worldwide, regional, and country wide comparison. The user may view an investigator's performance for a particular key performance indicator, as well as, view an investigator's performance against the performance of other investigators.

The user interface may include a list of filters. The list of filters may be displayed on the left panel of the user interface. The filters panel may include a data source filter, a therapeutic area filter, an indication filter, a program filter, a study phase filter, a region filter, a study type filter, and a study randomizer filter. In some implementations, the filter panel may include a subset of these filters, and in some implementations, the filter panel may include any other suitable filters. The end user may use a drop down selection tab to indicate which filters should be activated to generate the ranked list of investigators. For example, the end user may select what countries and/or what other geographical locations should be included in the dataset for determining the ranked list of investigators. For the example illustrated in FIG. 4, the end user selected all the states and cities of the United States to be included. The user interface illustrates a map of the selected geographical location with one or more push pins that indicate the overall scores of investigators across the selected geographical region. In some examples, a push pin may be used to identify the geographical location of the top ranked investigators based on the user selected filters. The size and color of the push pin used to identify the geographical location may be selected by the user. The user interface may also include a ranked list of investigators that reflects the data illustrated in the map. The ranked list may include details for each of the one or more investigators listed. For example, the list may include the investigator name, the geographical location of the investigator, the generated performance indicator score for the investigator, the scores for each of the one or more key performance indicators evaluated, and the experience of the investigator. In some implementations, the investigator's details may include the investigator contact information, and may include the option to add an investigator to a roster schedule. In some implementations, the user may select to rank the investigators based on one more key performance indicators scores. For example, the user may select to rank investigators based the score for both the screening rate and protocol violations key performance indicators. In another example, the user may select to rank the investigators by an overall performance indicator score and the score for screening rate.

The end user may have the ability to select a particular investigator from the ranked list to view further details about the selected investigator. In some implementations, the details may include the specialty area of the investigator, the IDN affiliations of the investigator, and the list of colleagues of the selected investigator that are affiliated with the same IDN network. In some implementations, the details may include a list of key performance indicators that were used by the computing systems at the analytical interface to generate the performance indicator score for the investigator.

Figure 5:
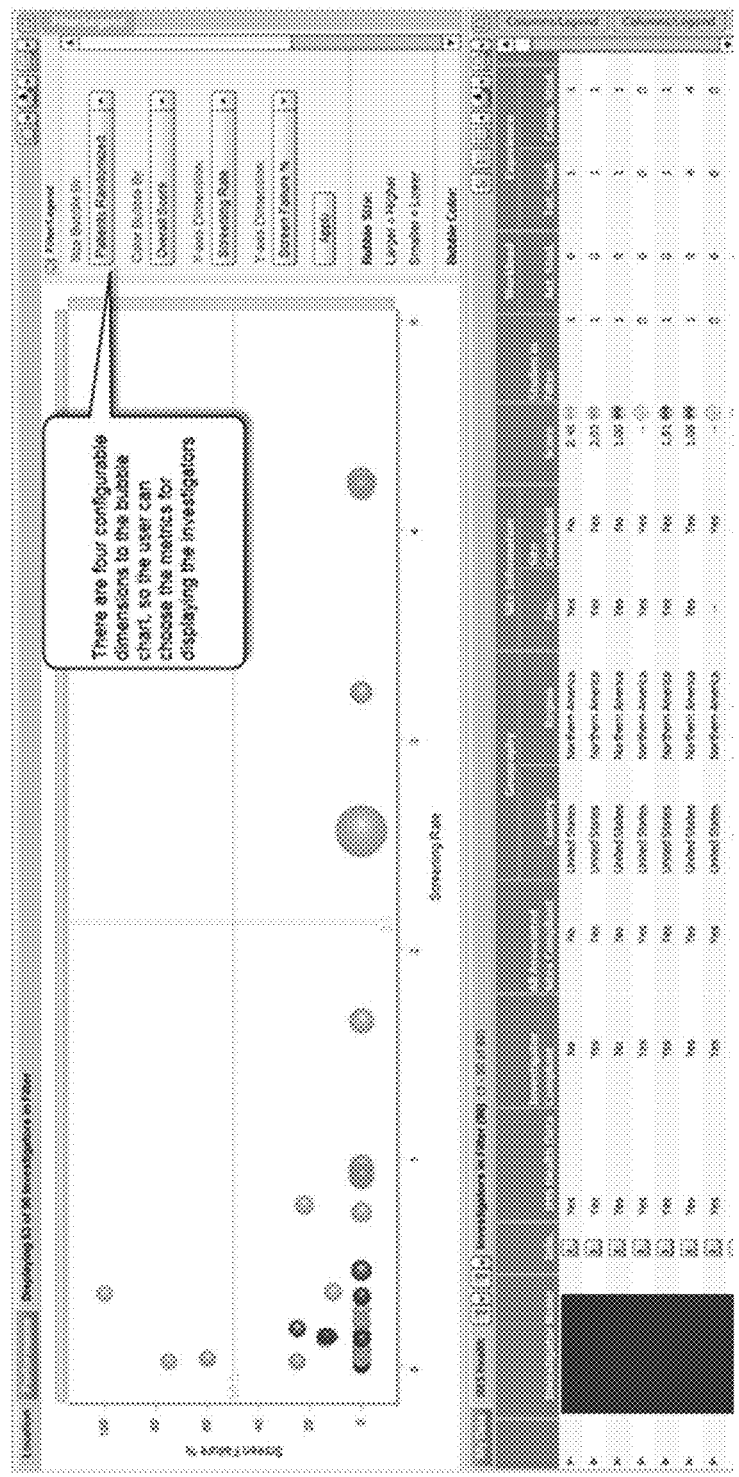

FIG. 5 illustrates an example user interface for user interaction with an application of a performance indicator offering. Interface 500 may be displayed when a user logs into a secure connection with the performance indicator application offering. The user may log into the application by providing a user specific user name and password, or any other suitable user authentication mechanism. The webpage may be specific to individual users of the application, that is, the webpage generated is specific to the user. The user interface 500 may be displayed when the user selects a performance tab on the task bar.

As illustrated in FIG. 5, the computing systems at the analytical infrastructure may display a bubble chart based on an evaluation of investigators. The results may be displayed in any suitable type of chart. In some implementations, the user interface may display the overall score determined for each investigator as a ranked list. The user may have the ability to configure the results to be displayed in a chart. As illustrated in interface 500, the user interface may include a task pane that includes one or more configurable dimensions. The user may select through drop down task bars, the x-axis dimension of the chart, the y-axis dimension of the chart, the color of the bubbles used on the chart, and the bubble size. For the example illustrated, the user selected the bubble size to indicate the number of patients randomized, the color of the bubble to indicate the overall score for an investigator, the x-axis to indicate the screen rate and the y-axis to indicate the screen failure percent. The user selected metrics are then used by the computing systems at the analytical infrastructure to generate a bubble chart. The bubble chart clearly depicts the received data for each investigator and allows the user to manipulate the data that is plotted to get a true understanding of each of the key performance indicators that were used to evaluate an investigator.

Figure 6:
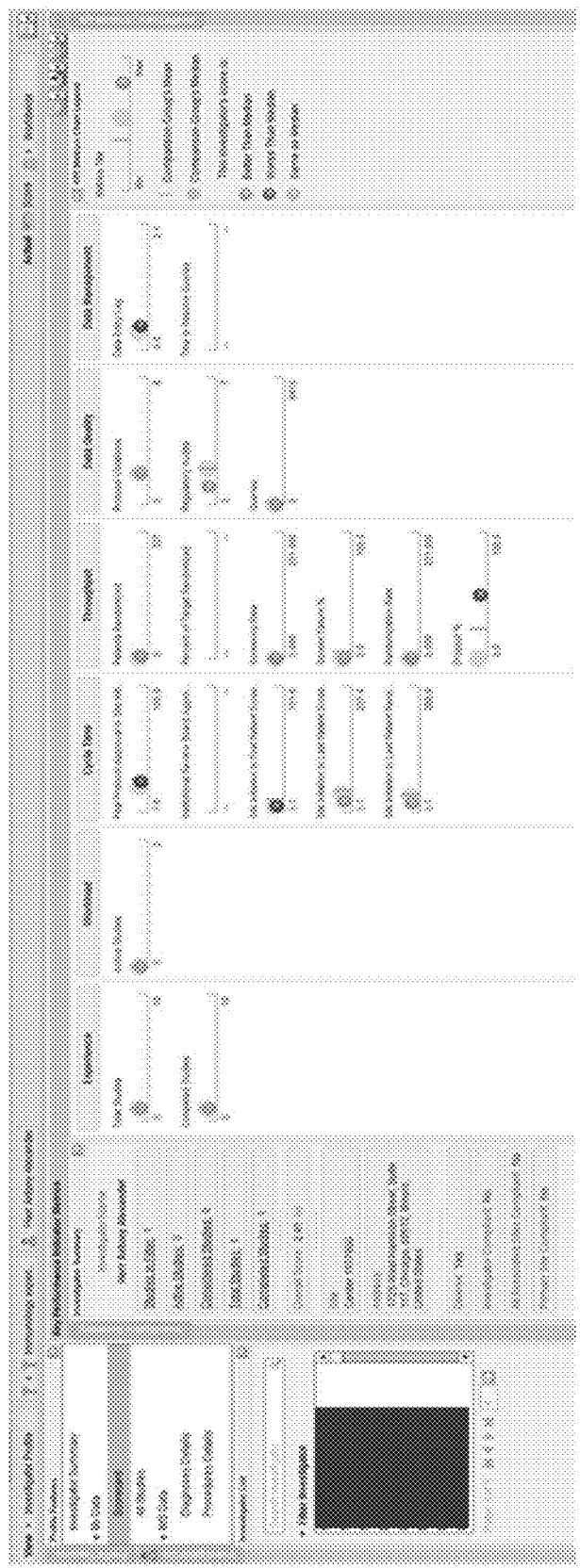

FIG. 6 illustrates an example user interface that may be displayed when a user selects an individual investigator from the ranked list of investigators. The user interface 600 displays the investigator's score card that includes the one or more metrics used to determine the overall performance indicator score for the selected investigator. The investigator score card may include the score determined for each key performance indicator used to determine the overall performance indicator score. The score card may include the investigator details such as the investigator name, address, therapeutic area, IDN affiliation, or any other suitable detail. The score card may also include the investigator performance relative to aggregate metrics for the comparison group like minimum/maximum/median/mode. In some implementations, the set of clinical trial studies used for the computation of scores for the one or more key performance indicators may be dynamically altered. For example, the data gathered from one or more clinical trial studies may be excluded from the analysis. In some implementations, the investigator performance is compared relative to all investigators across the selected geographical area. In other implementations, the investigator performance is compared relative to a worldwide group of investigators. The user may have the ability to select the comparison group using the web-based application.

Figure 7:
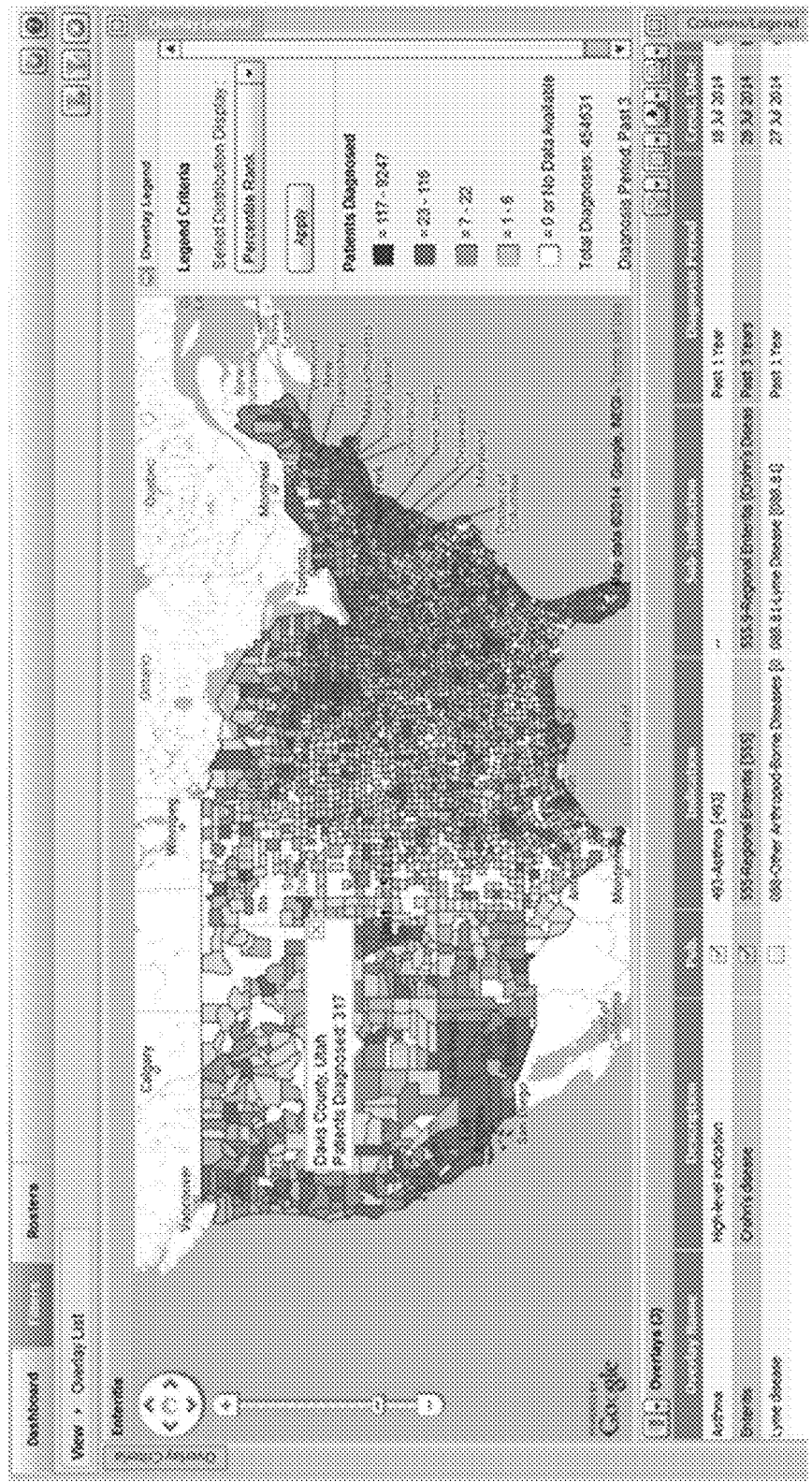

FIG. 7 illustrates a user interface 700 that may be displayed when a user of the performance indicator offering selects the overlay view. The computing systems at the analytical infrastructure may integrate the historical clinical trial data with prescription data, patient data, and insurance claims data. As illustrated in interface 700, the computing systems at the analytical infrastructure, may use the integrated data sources to produce a heat map. The heat map may display, for a selected geographical area, the patient diagnoses for a selected time frame. In some implementations, the heat map may display the patient diagnosis data for an entire country. The computing systems at the analytical infrastructure may use one or more different colors or shade of colors to represent the one or more different patient diagnoses ranges. In some implementations, the heat map may be displayed according to percentile rank. For the example illustrated, four patient ranges are used to represent the $1$-$25^{th}$, $26$-$50^{th}$, $51^{st}$-$75^{th}$ and $76^{th}$-$100^{th}$ percentiles. In some implementations, the patient ranges may represent any suitable diagnosis percentiles. The user interface may also include a list of diagnoses that a user may scroll through and select for which diagnosis the heat map should be displayed for. For the example illustrated in FIG. 7, the user selected the diagnosis Enteritis for the period of the past three years. The computing systems at the analytical infrastructure may indicate on the map, the geographical location with the highest number of patient diagnoses. The patient diagnosis information may be granular, and may display patient diagnosis data on a county by county basis.

Figure 8:
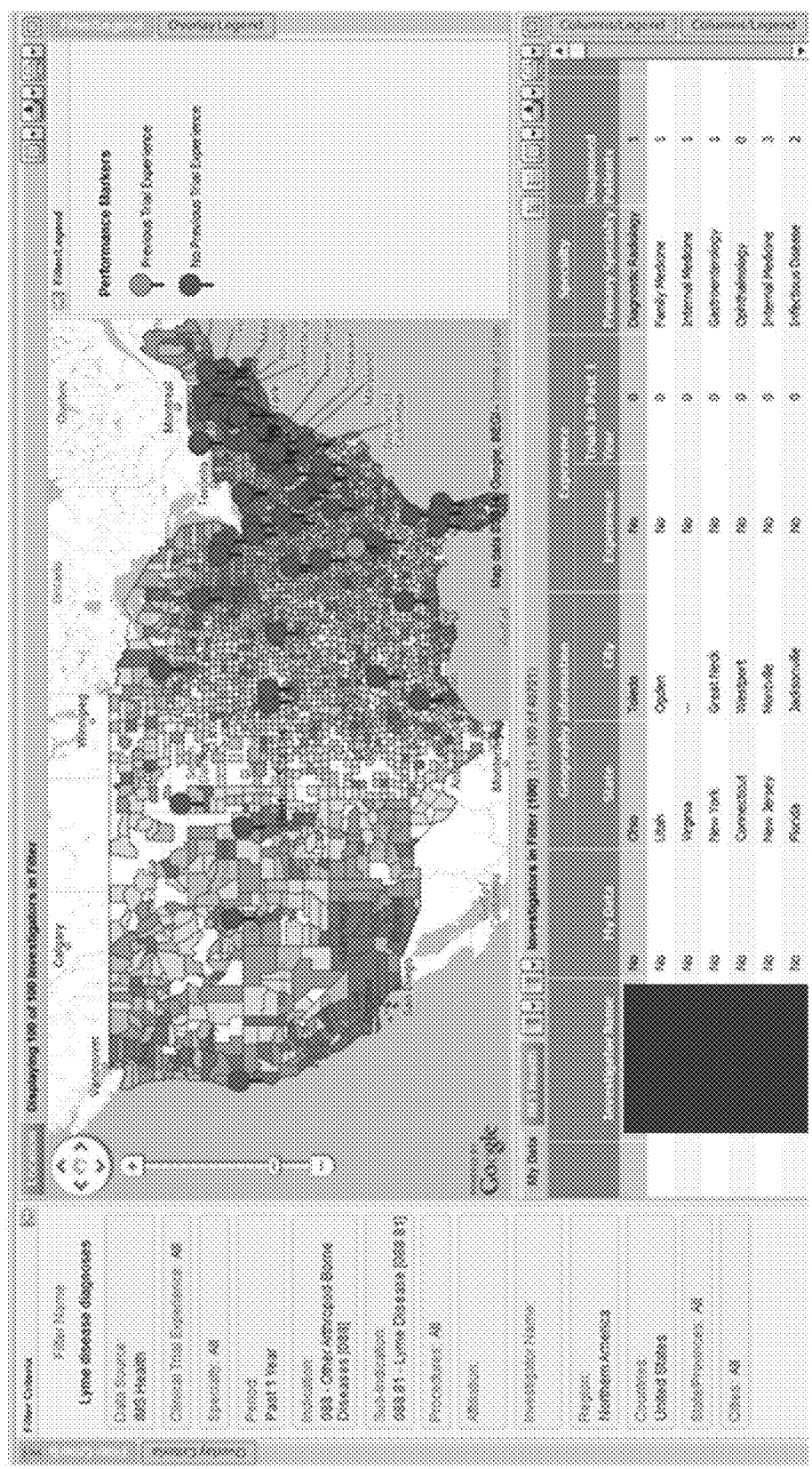

FIG. 8 illustrates an example user interface 800 that may be displayed when a user of the performance indicator offering selects to view data for a particular diagnosis within the received health records data. In some implementations, the health records data may include health insurance claims data, patient data, and prescribing data. The user may select which data set to mine to display diagnosis data. For example, the user may select to view diagnosis data from only health insurance data. The user may select an indication, a sub-indication, and a time interval for the data to be displayed. For the example illustrated, the user selected the indication "other arthropod borne diseases" and selected the sub-indication "Lyme disease." The computing systems at the analytical infrastructure may generate a map to illustrate a list of investigators that have made diagnoses of the user selected diagnosis. For the example illustrated in FIG. 8, the computing systems may generate a ranked list of investigators based on the selected diagnosis. The map illustrated may also indicate the location of the investigators on the ranked list. The geographical location of the ranked investigators may be indicated on the map with marker. The marker may also indicate the clinical trial experience of the investigator. In some implementations, the marker may indicate the investigators experience by the color of the marker. The ranked list of the investigators may be displayed below the generated map. The ranked list of investigators may list the name of the investigator, the city and or state of the investigator, the investigator specialty, the investigator clinical trial experience, and the number of patients the investigator diagnosed within the user selected time period.

In some implementations, the ranked list may include the number of clinical trials the investigator participated within the last year, and an indication whether the investigator has participated in a clinical trial carried out by the clinical trial organization associated with the user.

In some implementations, the user may narrow the list of investigators by applying one or more different filters to the search criteria. For example, the user may indicate, using a filter, to have only investigators with an overall performance score over a predetermined threshold be displayed. In some implementations, the user may select to display a ranked list of investigators based on the score for a particular key performance indicator. For example, a user may select to rank the investigators based on the key performance indicator of completed studies. In some implementations, the computing systems may generate the ranked list of investigators based on a universal data set. The universal data set may include all data sets available to the computing systems at the analytical infrastructure. In these implementations, the user may have the ability to identify the intersection of investigators from the organization's internal data set and the health records data received at the analytical infrastructure.

In some implementations, the user may select an investigator from the list of ranked investigators and select to view the diagnosis details for the investigator. The computing systems at the analytical infrastructure may generate a diagnosis bar chart that displays the number of patients diagnosed with the user selected diagnosis each month. The user may have the ability to select to display the diagnoses based on the age of the patient diagnosed. The data may be displayed for a user selected time period. For example the user may select to have the data displayed for the last year, or last two years. The diagnosis chart may also break down the diagnoses based on the gender of the patient.

Figure 9:
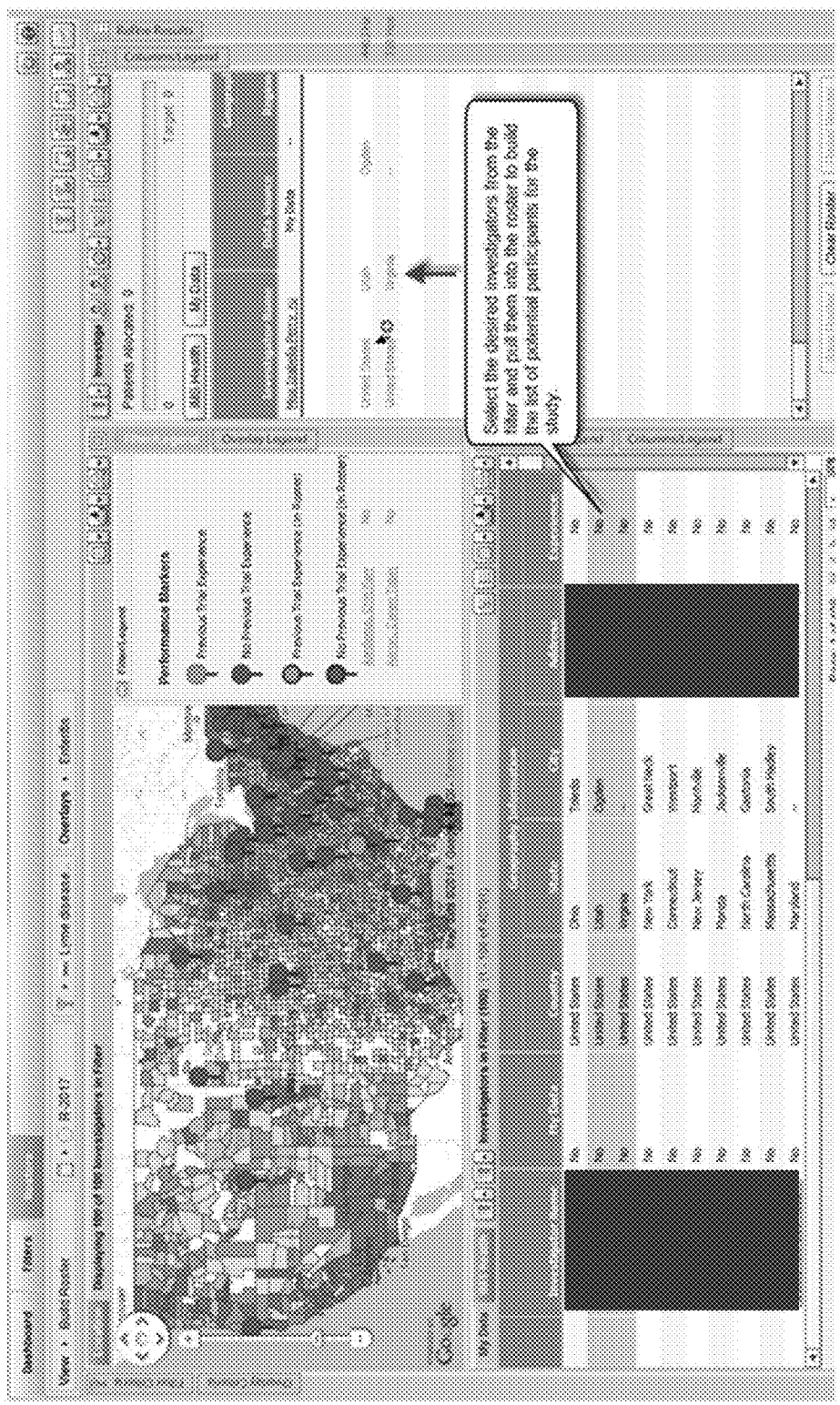

FIG. 9 illustrates an example user interface 900 that may be displayed when a user of the performance indicator offering selects to create a roster. The roster may be used to list the investigators selected by the user to participate in a clinical trial. The user may select the desired investigators from the list of ranked investigators into the roster drop down to build the list of potential participants for the clinical trial study. In some implementations, when the user adds an investigator to the roster the investigator is identified on the map by a marker. In some implementations, the computing systems at the analytical infrastructure may automatically generate a roster of investigators by selecting the top ranked investigators. In some implementations, when a user selects to have investigators ranked by a particular key performance indicator, the computing systems at the analytical infrastructure may generate a roster based on all investigators that records include data related to the particular performance indicator. In some implementations, the computing systems at the analytical infrastructure may communicate with the computing systems associated with investigators. In these implementations, when an investigator is placed in the roaster of investigators, the computing systems at the analytical infrastructure may communicate the inclusion in the roster to the investigator.

Figure 10:
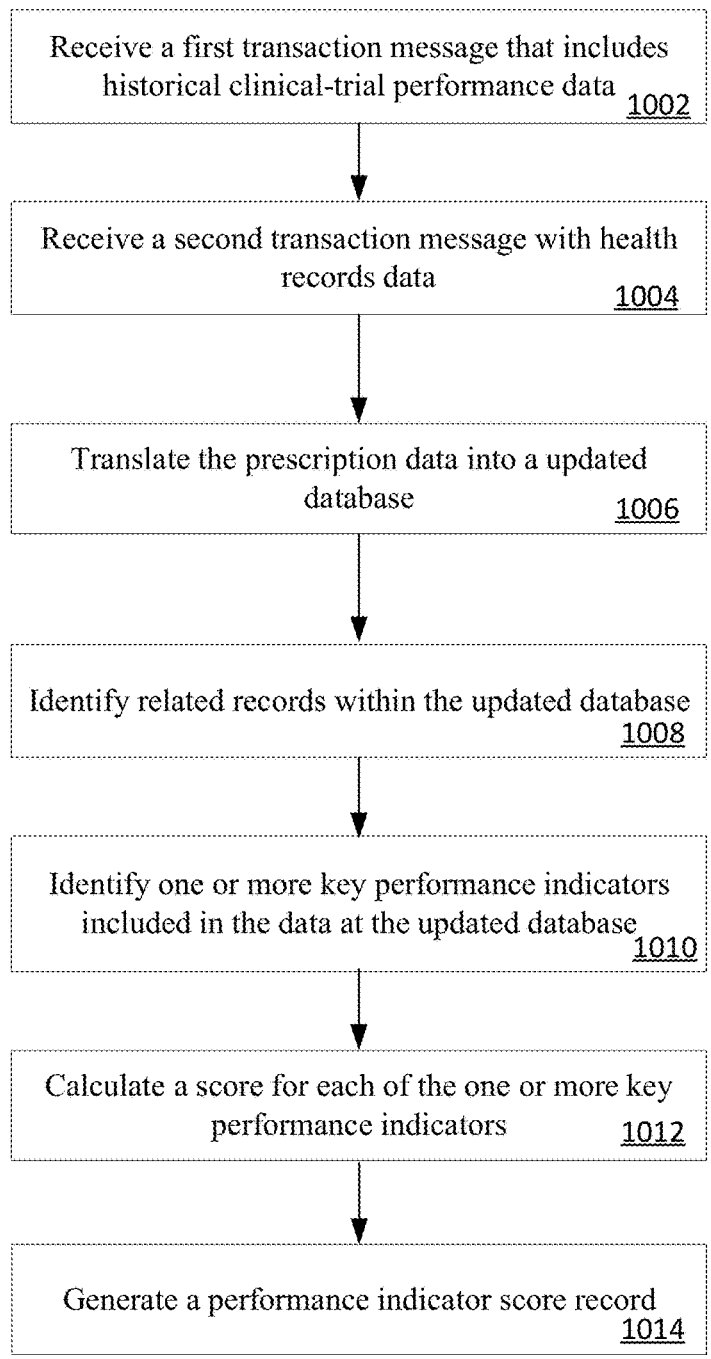
FIG. 10 is a flow chart of an example process for generating a performance indicator score record.

FIG. 10 is a flow chart of the process for generating a performance indicator score record. The computing systems at the analytical infrastructure receive a first transaction message that includes historical clinical trial performance data from one or more processors at a clinical research organization (1002). The received data file may be stored at a one or more databases at the computing systems at the analytical infrastructure. The transaction message received may be a data file, a stream of data, or a datagram. The historical clinical trial performance data may be data collected and maintained by one or more processors at a clinical research organization. The historical data may include detailed data of clinical trial studies carried out in the past by the clinical research organization. The historical clinical trial performance data may include the number of patients that participated in a clinical trial, the start date of the clinical trial, the completion date of the clinical trial, the number of days a physician took to response to a query, and any other suitable historical clinical trial data collected. The historical clinical trial data may be communicated to the computing systems at the analytical infrastructure on a periodical basis. For example, the historical data may be received at the computing systems of the analytical infrastructure every week, once a month, or quarterly. The historical data may be received at the computing systems of the analytical infrastructure at any suitable period. In some implementations, the one or more processors at the clinical research organization may communicate the historical data to the computing systems on a daily basis.

The computing systems at the analytical infrastructure receive a second transaction message with health records data indicative of insurance claims data (1004). The transaction message received may be a data file, a stream of data, or a datagram. The received health records data may be stored at a one or more databases at the computing systems of the analytical infrastructure. The health records data received may include health insurance claims from a larger percentage of pharmacies across the United States of America. The health insurance data me be part of IMS health data. The IMS health data may include patient data, prescriber data, and health insurance claims data that represents a large percentage of global health care data. The health records data may include medical details for patients. The health records data may be anonymized data yet may be rich in details of gender, sex, age, diagnosis, and any other suitable patient details. The computing systems at the analytical infrastructure may receive health records data from one or more processors associated with one or more hospitals, treatment facilities, prescribing facilities, Integrated Delivery Networks (IDNs), one or more patient systems, one or more prescriber systems, and one or more payer systems.

The computing systems at the analytical infrastructure may translate the health records data and the received historical clinical trial performance data into an updated database based on the received historical clinical trial performance data (1006). The health records data received may be stored at one or more databases at the computing systems at the analytical infrastructure. The received historical clinical trial performance data may be stored at the one or more databases. The two data sources may be combined logically across databases or physically within the same database to form a universal data set that integrates the data sources. The integrated data sources may be stored as one or more updated databases. The updated database may be an extension to the one or more databases that store the health records data and/or the clinical trial data. The updated database may be a computational database. The updated database may have the processing capability to execute extensive computations and calculations. The updated database may perform extensive calculations and computations on the health records data and the clinical trial historical data sources at the updated database high processing speeds. The updated database may be an energy efficient and time efficient database. The updated database may process large amounts of clinical trial historical data and health records data at very high speeds. The updated database may have the processing ability to allow the calculations and computations carried out on the data sources at the updated database to be quick and effective. The computing systems at the analytical infrastructure may identify related record within the updated database (1008). Data associated with a particular investigator or physician may be identified in the data sources and tagged with an identifier. Data associated with a particular geographical area, diagnosis, or physician specialty may be identified in the data sources and tagged with an identifier.

The computing systems at the analytical infrastructure may identify one or more key performance indicators in the updated database (1010). The data processing module at the computing systems may field and/or mine the universal data for data that may be used as a key performance indicator. For example, the data processing module may identify clinical trial data that may have recently been received at the computing systems, with dates that align with the current dates, and may identify the data as belonging to a currently active study. The computing systems at the analytical infrastructure may identity currently active clinical trial studies as an active studies key performance indicator. The data processing module may identify data for related records with one or more key performance indicators. The related records may be related by diagnosis, geographical location, investigator or physician, or any other suitable relation. For example, for a particular investigator, which may be identified with an investigator tag, the data processing module may identify the time between the date when the final protocol was approved and the date the site initiated to identify the final protocol approved to site initiation key performance indicator.

The computing systems at the analytical infrastructure may calculate a score for each of the one or more key performance indicators (1012). The administrative user at the computing systems at the analytical infrastructure may establish a medium performance range for each identified key performance indicator. The data received and identified for each key performance indicator may then be compared, by the statistical analysis module, to the medium performance range established by the administrative user. In some implementations, the administrative user may indicate the start and end points of the medium performance range for each identified key performance indicator. In other implementations, the administrative user may enter two values to indicate the start and end points of the medium performance range in terms of percentiles. In these implementations, the administrative user provides a ranking that is relative to other investigators. In some implementations, the performance indicator offering may be adapted to allow an end user to establish a medium performance range for each key performance indicator. The statistical analysis module at the computing systems may assign a score to the key performance indicators. In some implementations, the score assigned to the one or more identified key performance indicators may be a high score of 3, a medium score of 2, or low score of 1. In some other implementations, any other suitable score range may be used.

The computing systems at the analytical infrastructure may generate a performance indicator score record (1014). In some implementations, the administrative user may determine which of the one or more key performance indicators may be used to assess the performance of an investigator. In some implementations, the end user may have the ability to identify which key performance indicators should be used to generate the performance indicator score record for a particular investigator. The end user may select that the performance indicator score record be generated based on one key performance indicator. For example, the end user may select to have the performance indicator score based on the score assigned to the total studies key performance indicator. In these examples, the computing systems at the analytical infrastructure may generate a performance indicator score record, and rank one or more physicians based on the total studies key performance indicator, that is the number of clinical trial studies the physician has participated. In some implementations, the end user may select that the performance indicator score record be generated based on one or more key performance indicators. In these implementations, the end user may have the ability to identify the one or more key performance indicators that should be used to generate the performance indicator score record. The computing systems at the analytical infrastructure may generate the performance indicator score record for a particular investigator based on a weighted average of the one or more identified key performance indicators. The weight to each of the one or more key performance indicators may be assigned by the administrative user. In other implementations, the weight to each of the one or more key performance indicators may be assigned by the end user. In some implementations, the computing systems at the analytical infrastructure may generate a performance indicator score record for a particular investigator based on an algorithm. In some implementations, the end user may select which key performance indicators should be included in the calculation of the performance indicator score record for a particular investigator, or group of one or more investigators.

In some implementations, the performance indicator score record may be based on a therapeutic area. In these implementations, the weight of a particular key performance indicator may be evaluated differently based on the therapeutic area. For example, a clinical trial organization may decide that in a Respiratory clinical trial study, a monthly screening rate of fifteen or more patients is considered a high performance, whereas in an Oncology clinical trial study, a screening rate of five or more patients is considered a high performance. In some implementations, the end user may select to determine the performance indicator score for one or more investigators based on one key performance indicator. In these implementations, the computing systems at the analytical infrastructure may present the score of the selected key performance indicator as the performance indicator score record for the investigator.

The computing systems at the analytical infrastructure may rank one or more investigators/physicians based on the generated performance indicator score. The computing systems at the analytical infrastructure may rank one or more physicians based on the user selected key performance indicators and may generate a ranked list. The ranked list of investigators may be displayed to the user through the performance indicator tool application. In some implementations, the one or more investigators may be ranked based on a performance indicator score generated from the evaluation of one key performance indicator. In these implementations, the end user may select a single key performance indicator that the one or more investigators should be ranked according to. In some other implementations, the one or more investigators may be ranked based on a performance indicator score generated from the evaluation of one or more key performance indicators. In these implementations, each of the one or more key performance indicators may be assigned a weight and the performance indicator score may be generated based on the weighted average of the one or more key performance indicators evaluated. The performance indicator score may be generated based on an algorithm that includes the one or more ley performance indicators. In some implementations, the user may select to rank the investigators both on the overall performance indicator score and the score for one or more key performance indicators.

FIGS. 11-14 illustrate example user interfaces of user interaction with an application (e.g., a webpage application) for generating a roster of investigators. In implementations of the present disclosure, the application obtains data related to a plurality of potential clinical trial investigators (e.g., physicians) from two or more data sets. For example, the application can obtain data from a proprietary data set such as, for example, a data set owned by a user of the application (e.g., an organization or business such as a pharmaceutical corporation), and from a third-party data set such as, for example, a data set compiled by a third-party data source (e.g., a health care information service such as IMS Health).

The proprietary data set can include, but is not limited to, clinical trial data created and maintained by an organization from previously performed clinical trials. For example, proprietary data can include lists of clinical trial investigators that the organization may have previously hired or researched for clinical trials. In addition, the proprietary data can include various attributes related to the listed investigators, for example, contact information, data from historical clinical trials performed for the organization, and internal performance metrics associated with the investigators (e.g., performance metrics generated by the organization based on historical clinical trial data from trials performed by the investigator for the organization).

The third-party data set can include, but is not limited to, clinical trial data obtained and maintained by third-party data source based on data related to clinical trials performed by multiple organizations, patient data, insurance data, physician data, and data from other appropriate data sources compiled by the third-party data source. For example, third-party data can include lists of physicians who have conducted or are eligible to conduct clinical trials. In some implementations, the third-party physician list includes all or most of the investigators know to the organization and many additional investigators (e.g., physicians) eligible to perform clinical trials. In addition, the third-party data can include various attributes related to the physicians, for example, contact information, professional information, performance metrics based on data from historical clinical trials performed for multiple organizations, proximity to patients (e.g., areas of high patient density), number and type of procedures performed, clinical trial experience (e.g., a total number of trials performed by the investigator over a defined period of time), specialties, relevant publications, etc.

In some implementations, data from the proprietary data set and the third-party data set are obtained from separate databases (e.g., a proprietary data database and a third-party database). For example, the application can access the proprietary data set from a user organization's database(s), and the third-party data set from one or more third-party database. For instance, an organization can lease access to the third-party data set, and can be provided access through a user account with the third-party.

Figure 11:
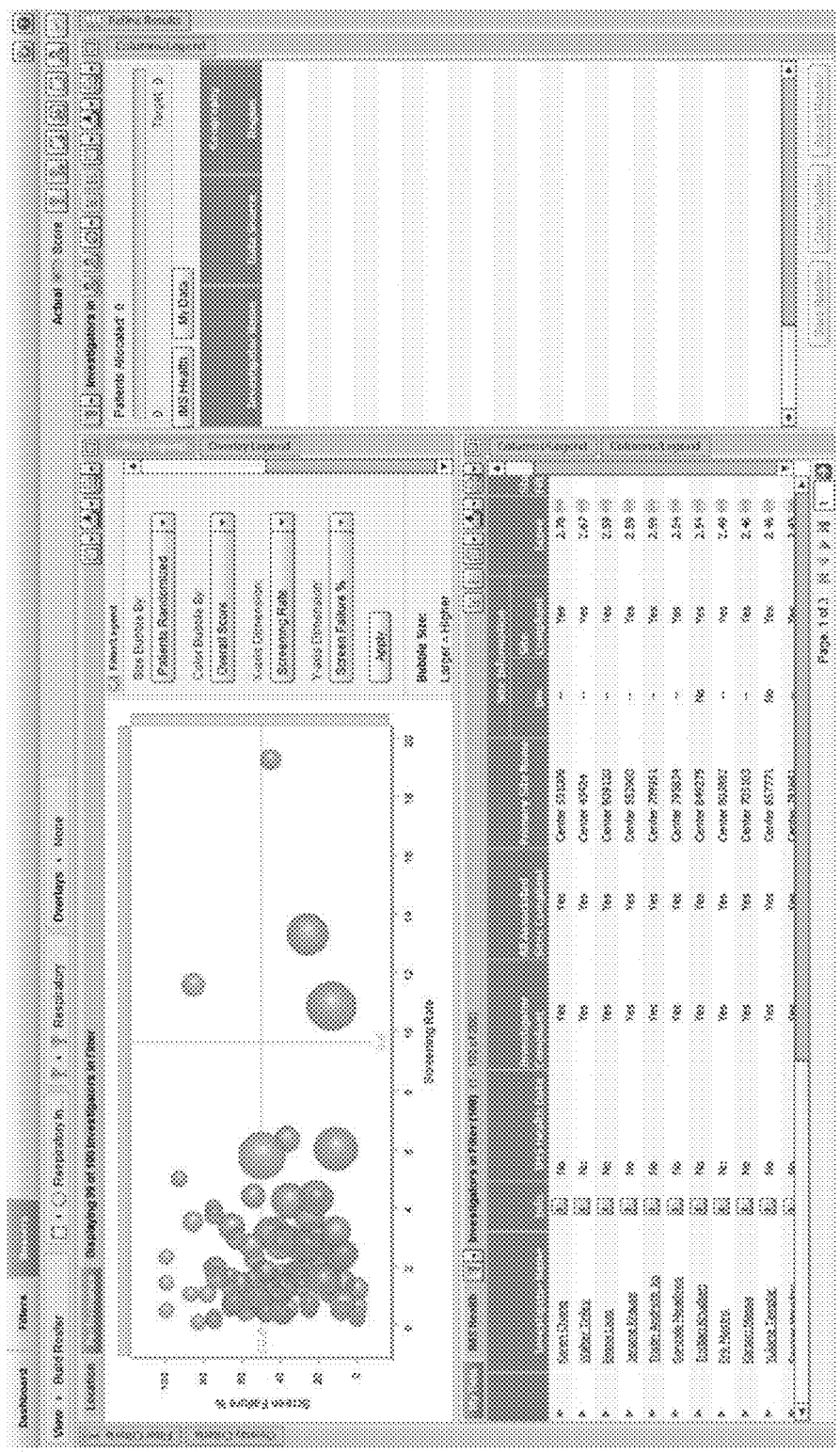
FIGS. 11-15 illustrate example user interfaces of user interaction with a webpage application for generating a roster of investigators.

FIG. 11 illustrates an example user interface 1100 for organizing potential investigators for inclusion in a clinical trial (similar to that shown in FIG. 5). The computing systems at the analytical infrastructure may display a multi-dimensional chart (e.g., a bubble chart) in the user interface 1100. The multi-dimensional chart may be a two-dimensional chart that represents three or more categories of data associated with a plurality of investigators. The multi-dimensional chart includes a plurality of icons (e.g., bubbles, circles, squares, or other icons) each representing an identity of an investigator. The computing systems at the analytical infrastructure may obtain data representing a set of attributes associated with each of the investigators, and represent several of the attributes along dimensions of the chart. The attributes may include, for example, identifying data for the investigator, key performance indicator scores, and/or raw data used to calculate key performance indicator scores. The icons represents attribute values associated with each investigator. The position of an icon along the x-axis represents a first attribute value, the position of the icon along the y-axis represents a second attribute value, and various graphical properties (e.g., size, shape, color) of the icon can represent additional attribute values associated with the represented investigator. For example, as depicted in the example user interface 1100, various attributes associated with each charted investigator may be represented by the position of each icon (e.g., along the x and y-axes), the size of the icon (e.g., the bubble size), and the color or shading of each icon (e.g., the bubble color). In some implementations, the user may select a subset of attributes associated with the represented investigators to be displayed in the chart. In the example shown the user has selected the attributes Patients Randomized, Overall Score, Screening Rate, and Screen Failure % to be represented in the chart.

The user may have the ability to configure the results to be displayed in the chart. As illustrated in interface 1100, the user interface may include a task pane that includes one or more configurable dimensions. The user may select investigator attributes to be represented by the chart dimensions and assign them to chart dimensions through drop down task bars. In the example shown, the user has designated Screening Rate to be represented by the x-axis dimension of the chart, Screen Failure % to be represented by the y-axis dimension of the chart, Overall Score to be represented by the color of the icons in the chart, and Patients Randomized to be represented by the icon size. The user selected metrics are then used by the computing systems at the analytical infrastructure to generate a multi-dimensional chart. The multi-dimensional chart clearly depicts the data for each investigator and allows the user to manipulate the data that is plotted to get a true understanding of each of the key performance indicators that were used to evaluate an investigator.

Moreover, enabling users to define how various investigator attributes are represented along dimensions of the multi-dimensional chart may provide users with the ability to efficiently recognize the best and worst performing investigators according to criteria for the users' particular clinical trial. For example, the icons in the lower-right quadrant of the multi-dimensional chart shown in interface 1100 represent investigators having the highest screening rate along with the lowest screen failure percentage. Thus, a user may find the best potential investigators for a particular clinical trial by pairing desired investigator attributes with appropriate dimensions of the multi-dimensional chart. Similarly, the multi-dimensional chart may be used to identify potentially incorrect or problematic investigator data (e.g., outliers). For example, an outlier icon may indicate that some portion of the charted data associated with the outlier icon is incorrect, or that there is a potential problem with the investigator's work. In addition, some implementations of interface 1100 also may include crosshairs that divide the multi-dimensional chart to help facilitate efficient recognition of investigator performance. In addition, the crosshairs may include data labels that indicate their position within the multi-dimensional chart. For example, the vertical crosshair line indicates that it is positioned along the x-axis at a screening rate of 9.6. Similarly, the horizontal crosshair line indicates that it is positioned along the y-axis at a screen failure percentage of 50.0.

In some implementations, interface 1100 may include a user-selectable filtering input. The filtering input may permit a user to filter the investigators represented in the chart based on one or more attributes associated with the investigators. In some implementations, the filtered set of investigators may be further reduced by selecting additional filtering criteria in a Refine Results pane. In some implementations, the multi-dimensional chart may include zoom and/or pan features that allow the user to focus in on tight clusters of investigator icons (e.g., as shown in the lower-left quadrant of the chart).

Figure 12:
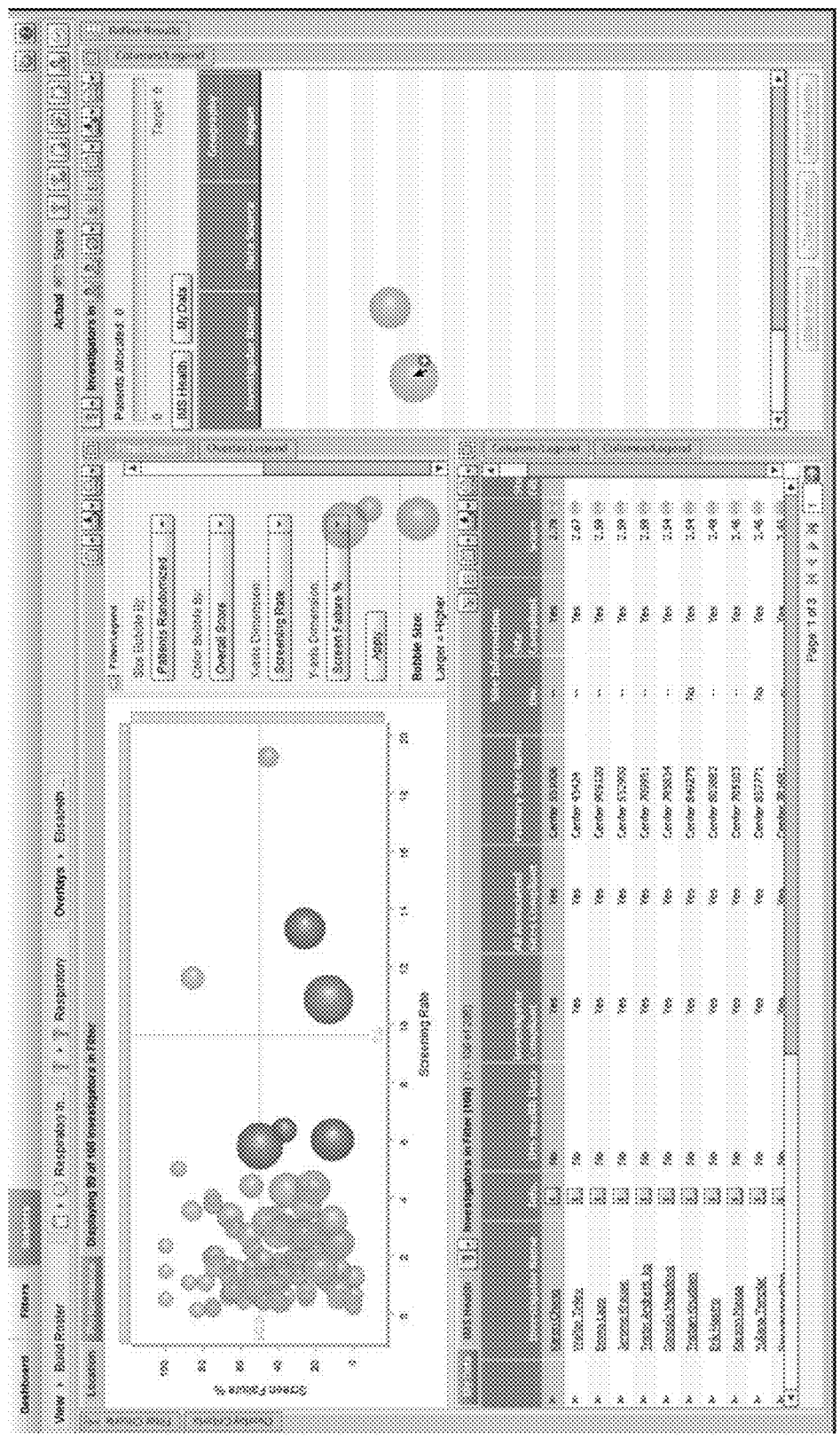
Figure 13:
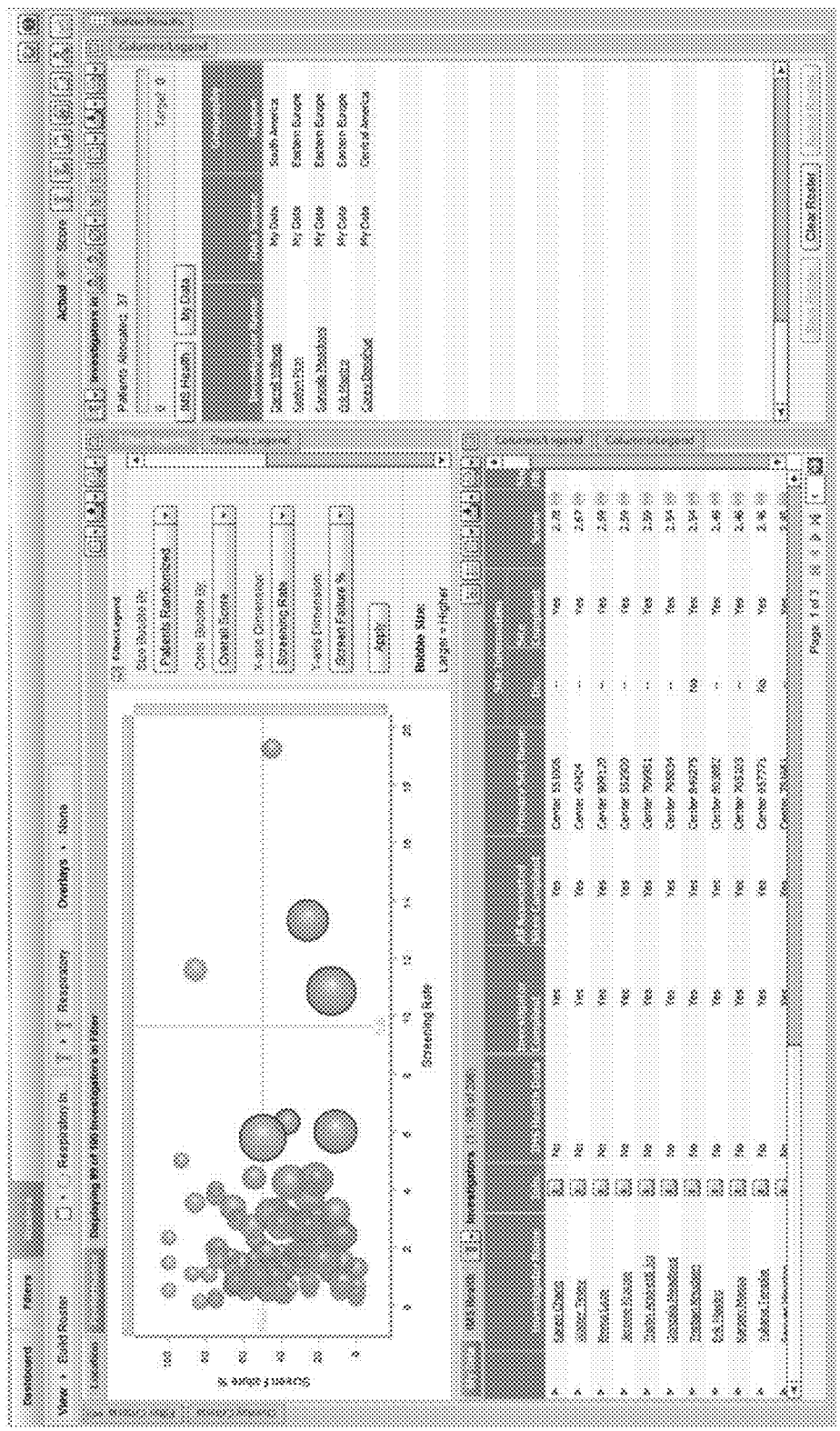

FIGS. 12 and 13 illustrate an example user interface 1200 for selecting investigators for inclusion in a clinical trial roster. The user interface 1200 includes a roster that may be used to list the investigators selected by the user to participate in a clinical trial. The user may select the desired investigators from the multi-dimensional chart. For example, in some implementations, a user may be permitted to select one or more of icons from the multi-dimensional chart and drag the selected icons into the roster. As shown in FIG. 13, once a selected icon has been dragged into the roster one or more attributes associated with investigator represented by the selected icon may be displayed in the roster (e.g., Investigator Name, Data Source, and Region). In some implementations, when the user adds an investigator to the roster the appearance of the investigator's icon is modified in the chart. The modification to the investigator's icon may include, for example, shading, highlighting, outlining, hatching, etc. For example, the icons associated with the selected investigators (e.g., Darrell Willings, Kaeln Pinn, Gonzalo Meados, Erik Mastro, and Corey Donahue) are outlined in red.

In some implementations, the computing systems at the analytical infrastructure may modify one or more attributes associated with the selected icons in response to the icons being added to (or removed from) the roster. For example, a considered studies attribute may be incremented (or decremented) when an associated icon is added to (or removed from) the roster. In some implementations, the computing systems at the analytical infrastructure may communicate with the computing systems associated with investigators. In these implementations, for example, when an investigator is placed in the roster, the computing systems at the analytical infrastructure may communicate the investigator's inclusion in the roster to the investigator (e.g., by e-mail). In some examples, the computing systems at the analytical infrastructure may communicate the investigator's inclusion in the roster to the investigator until the user indicates that the roster is complete, for example, by approving the roster. In some implementations, the roster may be approved by another user (e.g., a supervisor of the user or administrator).

Figure 14:
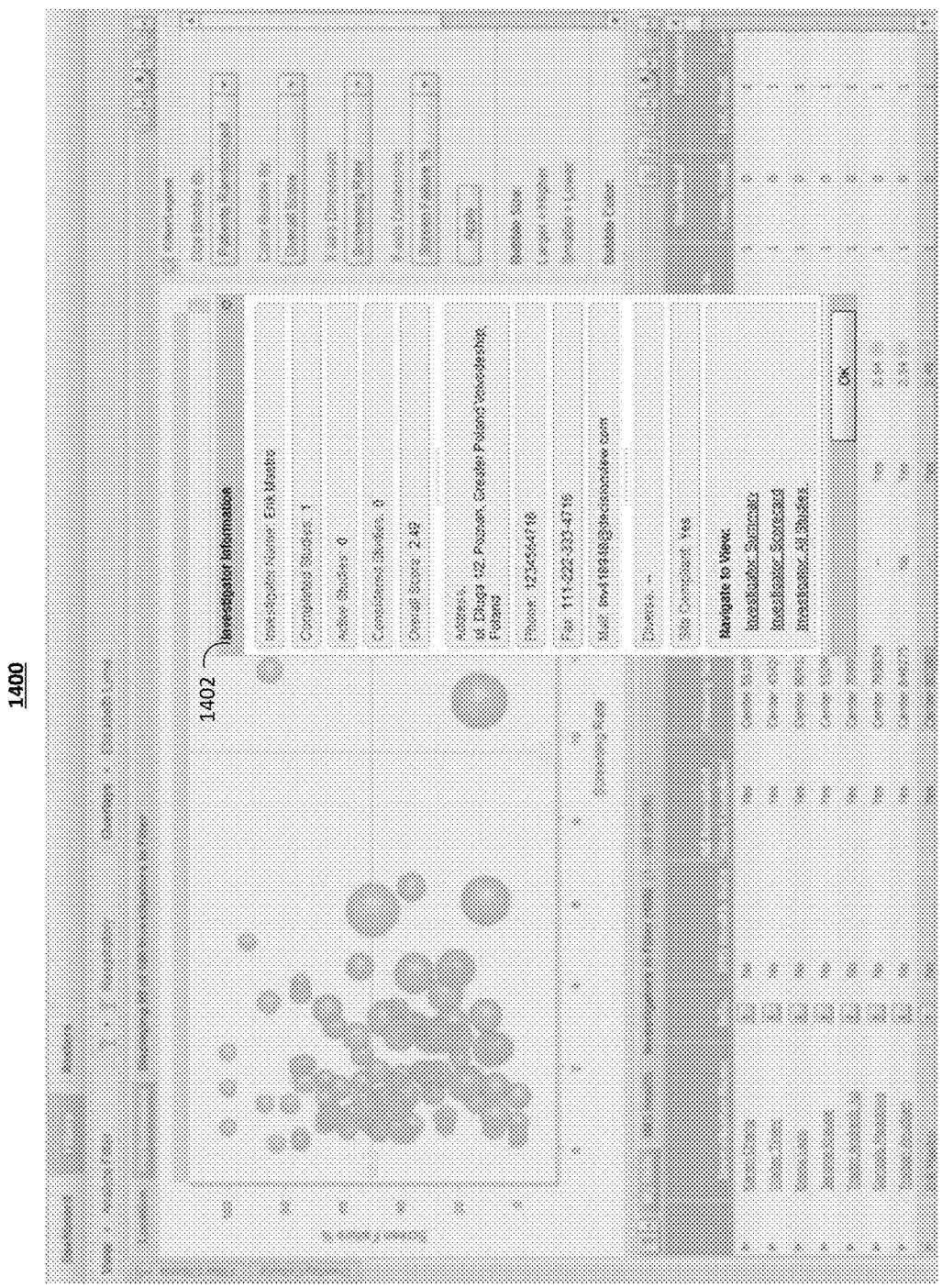

FIG. 14 illustrates an example user interface 1400 for organizing potential investigators for inclusion in a clinical trial including an investigator information display 1402. In some implementations, an investigator information display 1402 may be presented to a user when the user interacts with the icons displayed in the multi-dimensional chart. For example, if a user interacts with a particular investigator's icon, an investigator information display including attributes associated with the investigator (e.g., investigator Erik Mastro) may be presented to the user. A user interaction causing the investigator display to be presented may include hovering over an icon with a user selection device (e.g., a mouse or touchpad cursor) or selecting an icon (e.g., clicking an icon or touching an icon on a touchscreen).

Figure 15:
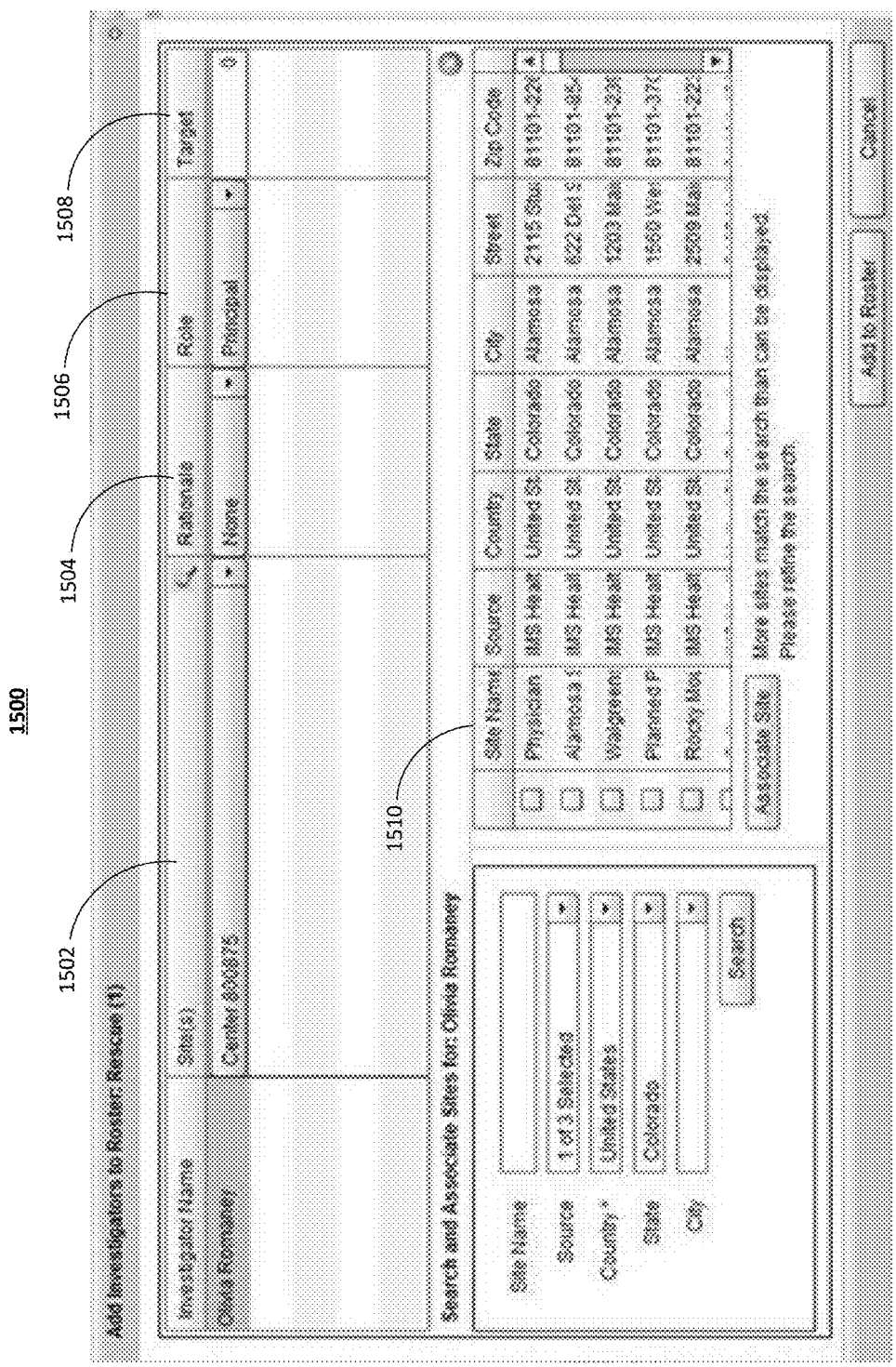

FIG. 15 illustrates an example user interface 1500 for modifying attributes of investigators included in a clinical trial roster. In some implementations, an interface 1500 may be presented to a user when the user selects an investigator identity displayed in the clinical trial roster. A user may be permitted to select various attributes associated with the selected investigator's (e.g., Olivia Romaney) participation in a clinical trial. For example, the user may select an investigation site at which the investigator should perform their clinical trial work 1502, a rationale for choosing the investigator to participate in the trial 1504, a role that the investigator is expected to play in the trial 1506, and a target number of patients that the investigator is expected to examine for the trial 1508. In some examples, the interface 1500 may include a list 1510 of potential investigation sites for the investigator to perform their clinical trial studies. The list 1510 may include sites near the investigator, sites at which the investigator has admission privileges, sites preferred by the user, or sites with specific equipment or facilities required for the trial. In some implementations, the list may include only sites meeting a user selected filter criteria, for example, to limit the listed sites to only those relevant to the user's clinical trial.

Figure 16:
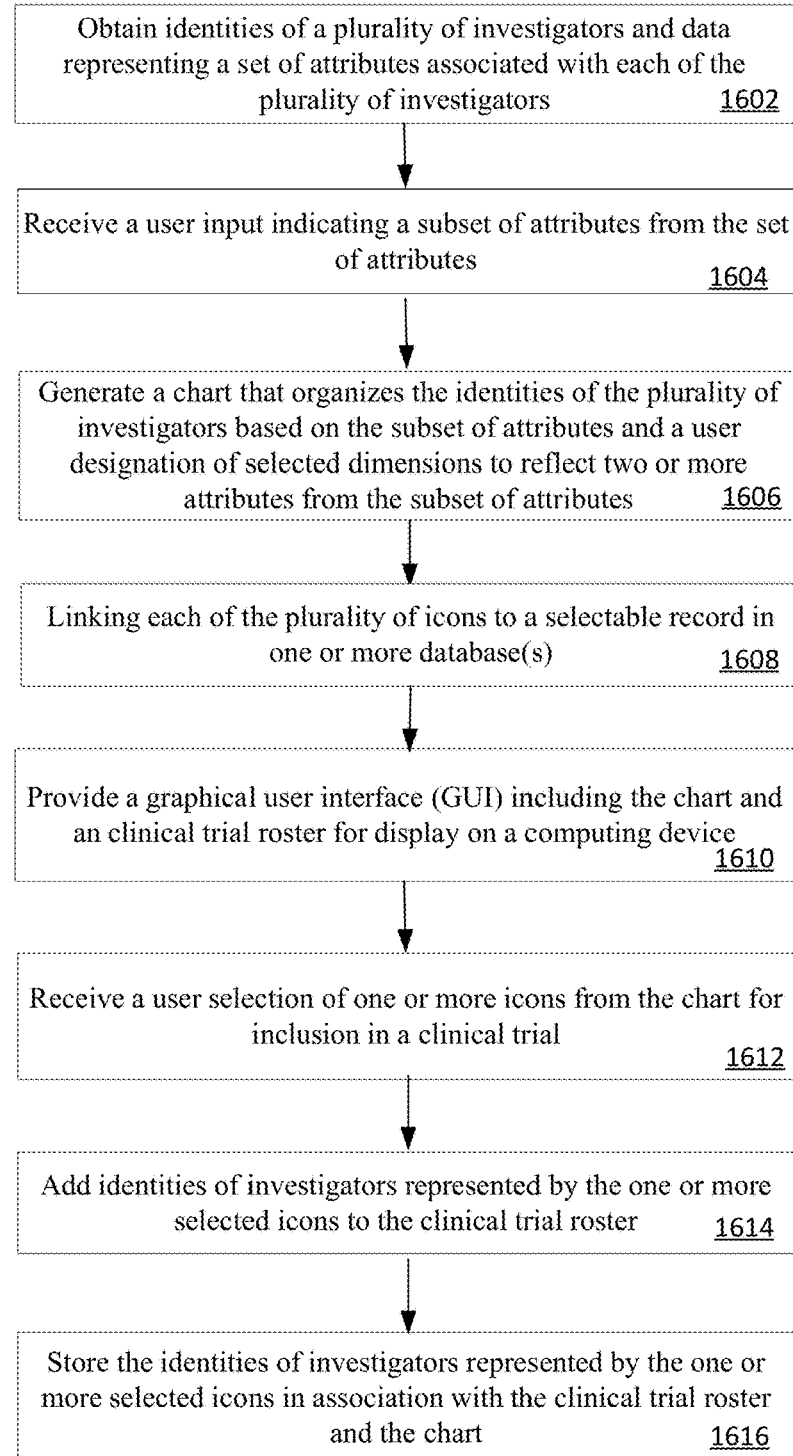
FIG. 16 is a flow chart of an example process for generating a user interface for generating a roster of investigators.

FIG. 16 is a flow chart of an example process 1600 for generating a user interface for generating a roster of investigators. In some examples, the example process 1600 can be provided as one or more computer-executable programs executed using one or more computing devices. In some examples, the process 1600 is executed by a computing systems at an analytical infrastructure. In some examples, the process 1600 may enable more efficient use and organization of investigator data, and thereby, reduce the computing resources required to both maintain and process investigator data, and to coordinate logistics related to organizing investigators for clinical trials.

The computing systems at the analytical infrastructure obtain identities of a plurality of investigators and data representing a set of attributes associated with each of the plurality of investigators from a database (1602). For example, the identities of a plurality of investigators and data representing a set of attributes associated with each of the plurality of investigators is obtained from two or more data sets. For example, the identities and associated data can be obtained from a proprietary data set such as, for example, a data set owned by a user of the application (e.g., an organization or business such as a pharmaceutical corporation), and from a third-party data set such as, for example, a data set compiled by a third-party data source (e.g., a health care information service such as IMS Health). The attributes associated with each of the plurality of investigators may include, for example, identifying data for the investigator, key performance indicator scores, and/or raw data used to calculate key performance indicator scores. Identifying data for investigators may, for example, include data such as name, contact information, and medical specialty. Raw data may include, for example, historical clinical trial data and health records data used to calculate key performance indicator scores.

Additionally, for example, the proprietary data set can include, but is not limited to, clinical trial data created and maintained by an organization from previously performed clinical trials. For example, proprietary data can include lists of clinical trial investigators that the organization may have previously hired or researched for clinical trials. In addition, the proprietary data can include various attributes related to the listed investigators, for example, contact information, data from historical clinical trials performed for the organization, and internally computed key performance indicator scores associated with the investigators (e.g., performance metrics generated by the organization based on historical clinical trial data from trials performed by the investigator for the organization).

Additionally, for example, the third-party data set can include, but is not limited to, clinical trial data obtained and maintained by third-party data source based on data related to clinical trials performed by multiple organizations, patient data, insurance data, physician data, and data from other appropriate data sources compiled by the third-party data source. For example, third-party data can include lists of physicians who have conducted or are eligible to conduct clinical trials. In some implementations, the third-party physician list includes all or most of the investigators know to the organization and many additional investigators (e.g., physicians) eligible to perform clinical trials. In addition, the third-party data can include various attributes related to the physicians, for example, contact information, professional information, key performance indicator scores based on data from historical clinical trials performed for multiple organizations, raw data associated with the key performance indicator scores, proximity to patients (e.g., areas of high patient density), number and type of procedures performed, clinical trial experience (e.g., a total number of trials performed by the investigator over a defined period of time), specialties, relevant publications, etc.

In some examples, data from the proprietary data set and the third-party data set are obtained from separate databases (e.g., a proprietary data database and a third-party database). For example, the application can access the proprietary data set from a user organization's database(s), and the third-party data set from one or more third-party database. For example, an organization can lease access to the third-party data set, and can be provided access through a user account with the third-party.

The computing systems at the analytical infrastructure receive a user input indicating a subset of attributes from the set of attributes associated with each of the plurality of investigators (1604). The user input may be received from a menu of attributes in a drop down task bar, for example. In some implementations, default attribute selections may be provided to a user, and the user may be permitted to alter the default attribute selections. The user input may, in some examples, include a designation chart dimensions to reflect the attributes.

The computing systems at the analytical infrastructure generate a multi-dimensional chart that organizes the identities of the plurality of investigators based on the subset of attributes and a user designation of selected dimensions to reflect two or more attributes from the subset of attributes (1606). The multi-dimensional chart may be a two-dimensional representation of a chart reflecting various investigator attributes along three or more dimensions. The investigator attributes represented by the dimensions of the multi-dimensional chart may include the user selected subset of attributes, and, in some examples, default attributes. For example, the multidimensional chart may be a bubble chart including a plurality of icons, where each icon represents an identity of one of the plurality of investigators. Each icon may be positioned on the multi-dimensional chart along an x-axis according to one user selected attributes of the represented investigator and along a y-axis dimension according to another user selected attribute of the represented investigator. A size of each icon (e.g., bubble) may represent a third attribute of the investigator represented by the icon, and a color of the icon may represent a fourth attribute of the investigator. The user input may, in some examples, include a designation chart dimensions to reflect the attributes, and the computing systems at the analytical infrastructure generate the multi-dimensional chart in accordance with such designations. For example, the user input may include a user designation that one attribute (e.g., a screening rate) is to be represented by a first dimension of the multi-dimensional chart (e.g., the x-axis) and that another attribute (e.g., a screen failure %) is to be represented a second dimension of the multi-dimensional chart (e.g., the y-axis).

The computing systems at the analytical infrastructure links each of the plurality of icons to a selectable record in a database (1608), and provides a graphical user interface (GUI) including the multi-dimensional chart and an clinical trial roster for display on a computing device (1610). The icons may be linked to associated database records so that the user interactions with ones of the plurality of icons cause one or more attributes associated with the ones of the plurality of icons to be altered within the database. For example, the linking can tie one or more values in either the proprietary data set, the third-party data set, or both to user interactions with the respective icons. For instance, in some implementations because the icons are linked to associated data set records the computing systems at the analytical infrastructure may modify an attribute associated with an investigator identity when the associated icon is added to the roster. In some implementations, the computing systems at the analytical infrastructure may modify attributes associated with investigator identities added to the roster when the roster is saved.

In some implementations, the modification of the attribute associated with an investigator identity may cause a linked icon in another multi-dimensional chart (e.g., one being viewed by a different user on a separate computing device) to be modified based on the modification to the attribute in one or more data set record(s). In other words, if a first user drags an icon for investigator Smith into the roster (and, in some examples, saves the roster) that interaction with investigator Smith's icon may cause one of investigator Smith's attributes to be updated an applicable data set, for example, an attribute related to the number of clinical trials for which investigator Smith is being considered (e.g., a Considered Studies attribute). When this Considered Studies attribute for investigator Smith is updated in the applicable data set(s), the computing systems at the analytical infrastructure may cause an attribute of investigator Smith's icon to change in a multidimensional chart being viewed by a second user. For example, if in the second user's chart the second user has defined that Considered Studies is to be represented by the icon size, the size of investigator Smith's icon may increase in response to the first user adding investigator Smith to the first user's roster. This update to the second user's chart may occur in real time (e.g., with minimal delays due to processing), on a system directed regular or irregular refresh of the second users interface, or a user triggered refresh of the second user interface.

The computing systems at the analytical infrastructure receives a user selection of one or more icons from the multi-dimensional chart for inclusion in a clinical trial (1612). For instance, the user may be permitted to drag and drop the icons into the roster. In response to the user selection, the computing systems at the analytical infrastructure adds identities of investigators represented by the one or more selected icons to the clinical trial roster (1614). In some implementations, the appearance of icons associated with selected investigators may be modified to indicate to users that the investigators have already been added to the roster. For example, the modification to icons associated with investigators added to the roster may include one or more of shading, highlighting, outlining, hatching, etc. In some implementations, as mentioned above, adding the icons to the roster may cause data set record(s) that are linked to the icons to be modified.

The computing systems at the analytical infrastructure stores the identities of investigators represented by the one or more selected icons in association with the clinical trial roster and the multi-dimensional chart (1616). For example, the user inputs, multi-dimensional chart, and attributes associated with selected investigators may be stored for later editing or as a read-only file to archive data for later review as needed during the clinical trial. In some implementations, the stored data may be compared to more recent data in order to help clinical trial administrators understand changes in investigator performance and/or the original rationale for roster decisions.

In some implementations, the process may include an approval step, in which a second user (e.g., a supervisor of the user or administrator) must approve a roster generated by the user. Roster approval may, for example, require authentication of the second user as having appropriate permissions to approve rosters generally or a roster for a specific trial. Approval may require the computing systems at the analytical infrastructure to validate one or more electronic credentials (e.g., a user name and password, one or more biometric credentials, an electronic ID, or other appropriate electronic credential) associated with the second user to authenticate the second user, and to establish the second user's permissions. In some implementations, the investigator identities, multi-dimensional chart, and clinical trial roster are not stored until the roster is approved.

In some implementations, the data set record(s) linked to icons of investigators who have been added to a roster may not be modified until the roster is approved. In some implementations, an additional attribute associated stored in the data set(s) and with investigators who are included in the roster may be modified when the roster is approved. For example, in such implementations when a user selects an icon associated with investigator Smith for inclusion in the roster, the selection of investigator Smith's icon causes one of investigator Smith's attributes to be updated in the appropriate data set(s), for example, an attribute related to the number of clinical trials for which investigator Smith is being considered. Subsequently, when the roster including investigator Smith is approved another attribute associated with investigator Smith may be updated in the data set record(s), for example, an attribute related to the number of active clinical trials for which investigator Smith is currently included.

In some implementations, a user may be permitted to select one or more attributes related to an investigator's participation in a clinical trial, for example, as described above in reference to FIG. 15. In such implementations, a user selection of the one or more attributes may be received and stored in associate with the investigator's identity. User selectable attributes may include, for example, an assignment of an investigation site for the examiner to perform clinical trial studies, a rationale for choosing the investigator to participate in a clinical trial, a role that the investigator is expected to play in a clinical trial, and a target number of patients that the investigator is expected to examine for a clinical trial. In some examples, an attribute related to the investigator may be altered in one of the linked data sets in response to receiving the user selection. In some examples, the user selections may be stored in association with the investigator's identity in the clinical trial roster.

In some implementations, when a roster is approved electronic notification (e.g., e-mail, text message, voice message, or other appropriate electronic message) can be sent to one or more of the investigators included in the roster using contact information for each investigator from the database. In some implementations, the electronic notification may require an investigator to confirm their availability for the trial and upon receiving the confirmation one or more attributes associated with the respective investigator may be updated in the database, for example, an attribute related to active clinical trials in which investigator is participating. In addition, the notification may include information related to an investigator's participation in the study, for example, an investigation site to which the investigator has been assigned for performing the clinical trial (e.g., a hospital, clinic, university, or other medical facility), or a target number of participants for the investigator's portion of the clinical trial. In some implementations, the notification may include user selectable inputs allowing an investigator to accept, decline, or suggest changes to information related to the investigator's participation in the clinical trial. For example, the investigator may be permitted to accept or decline participation in the clinical trial, and to suggest changes to the investigation site, target number of participants, or other criteria related to the investigator's participation in the clinical trial.

In some implementations, the computing systems at the analytical infrastructure may select a subset of identities from the plurality of investigators for inclusion in the multi-dimensional chart based on one or more user-selected filtering criteria. The user selected filtering criteria may include some or all of the attributes associated with the investigators. In some implementations, the computing systems at the analytical infrastructure may permit a user to filter investigator data based on multiple filtering levels. In some implementations, the computing systems at the analytical infrastructure may permit a user to select filtering criteria based on the data set to which the filtering criteria data is related. For example, a primary filtering criteria may be investigators included in the proprietary data set, and a secondary filtering criteria may include investigators included in the third-party data set. Thus, a user can identify overlapping data between the proprietary data set and the third-party data set.

In some implementations, a user may submit a previously assembled list of investigators (e.g., a previously generated clinical trial roster), and the computing systems at the analytical infrastructure may generate the multi-dimensional chart based on the investigators included in the submitted list. The previously assembled list may be a stored clinical trial roster (e.g., a draft roster or a roster from a different clinical trial). In some implementations, the roster may be persistent across various user interfaces. For example, a user may begin generating a roster while viewing the heat chart depicted in interface 900 of FIG. 9 and desire to further refine the roster based on the multi-dimensional chart depicted in interface 1100 or FIG. 11. In such an implementation, when the user choses to switch from interface 900 to interface 1100, the computing systems at the analytical infrastructure may generate the multi-dimensional chart based on the investigators included in the roster from interface 900. Some implementations may include a user selectable option to make the roster persistent or not persistent between multiple interfaces.

In some implementations, icons associated with investigators who have not yet performed a clinical trial or for whom no historical clinical trial data is available may be given a distinctive appearance (e.g., a distinctive color or shape). For example, icons associated with such investigators may be shaded grey.

Enabling user manipulation of large amounts of data from multiple data sets and relating disparate factors to identify extraordinary objects can require large amounts of memory and processing cycles. Considering each dimension of a database individually may reveal only modest differences between relative targets. Yet as disparate factors are related to one another and as a user is allowed to change analytic criteria in real time across large volumes of data, an administrator may be able to perceive a degree of persistency of desirable characteristics while also recognizing the relative suitability, oftentimes diminished, of other targets as the criteria and dimensions are modified. This persistency may become even more compelling when three or four dimensions of consistency are considered and an administrator is allowed to perceive targets of interest whose ordinal metric, under new criteria, may not surface into a display of top targets but for a user designation to maintain selected objects within a data view of legacy targets under the new criteria. While advances in computer technology have greatly increased the amount of available information, the sheer volume of information can be overwhelming and cumbersome to the extent that processors may struggle to operate on data sets in time such that a user can perceive the impact of new criteria in real-time. In some configurations, real-time is defined as the time required to maintain a TCP connection across a wide area network. In other configurations, real-time is defined as the ability to render a new display within a threshold degree of time (e.g., 1 second, 3 seconds, or 10 seconds). By configuring the database to perform preprocessing in a way that facilitates real-time updates to a display, the user is provided with an investigative tool that allows multidimensional target investigation in a manner capable of allowing a user to perceive the impact of a particular factor on relative performance.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS)

receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method for organizing clinical trial data executed by one or more processors, the method comprising:
 obtaining, by the one or more processors of a server system and from a selectable record in an aggregate database of the server system, identities of a plurality of investigators and data representing a set of attributes associated with each of the plurality of investigators from a first data set and a second data set, wherein:
  the first data set containing proprietary data associated with at least one of the investigators and received from a first set of databases,
  the second data set containing third-party data associated with at least one of the investigators and received from a second set of databases that is different from the first set of databases, and
  the selectable record enables the one or more processors to perform one or more adjustments to data of the identities of the plurality of investigators included within the aggregate database in a first time period that is shorter than a second time period for performing the one or more adjustments on data of the identities of the plurality of investigators included within the first set of databases and the second set of databases but not stored within the aggregate database;

receiving, by the one or more processors and from a computing device, a user input indicating a subset of attributes from the set of attributes associated with each of the plurality of investigators;

generating, by the one or more processors, a multi-dimensional chart that organizes the identities of the plurality of investigators based on the subset of attributes and a user designation of selected dimensions to reflect two or more of attributes from the subset of attributes, the multi-dimensional chart comprising:
  a first dimension representing a first attribute from the subset of attributes;
  a second dimension representing a second attribute from the subset of attributes; and
  a plurality of icons,
    each icon representing an identity of one of the plurality of investigators,
      wherein each icon is positioned on the multidimensional chart along the first dimension according to a value of the first attribute associated with the represented identity and along the second dimension according to a value of the second attribute of the represented identity, and
      wherein a graphical property of each icon represents a value of a third attribute of the represented identity;

linking, by the one or more processors, each icon included in the plurality of icons to the selectable record in the aggregate database so that user interactions with icons included in the plurality of icons by the computing device cause one or more attributes associated with the icons included in the plurality of icons to be altered within the aggregate database;

providing, by the one or more processors and for display on the computing device, a graphical user interface (GUI) including the multi-dimensional chart and a clinical trial roster;

receiving, by the one or more processors and from the computing device, a user selection of one or more icons from among the plurality of icons for inclusion in a clinical trial;

in response to receiving the user selection:
  adding, by the one or more processors, identities of investigators represented by the one or more selected icons to the clinical trial roster;
  updating, by the one or more processors, the selectable record to reflect that the identities of investigators represented by the one or more selected icons have been added to the clinical trial roster; and
  updating, by the one or more processors and based on linking each icon included in the plurality of icons to the selectable record in the aggregate database, one or more attributes in the selectable record that are associated with the one or more selected icons.

2. The method of claim 1, comprising:
in response to adding the identities of investigators represented by the one or more selected icons to the clinical trial roster, modifying, by the one or more processors, an attribute associated with at least one of the added identities; and
causing, by the one or more processors, a linked icon in another multi-dimensional chart to be modified based on the attribute associated with the at least one of the added identities being modified.

3. The method of claim 1, comprising selecting, by the one or more processors and based on user selected filtering criteria, a subset of identities of the plurality of investigators, and
  wherein generating the multi-dimensional chart comprises generating the multi-dimensional chart to organize the identities in the subset of identities of the plurality of investigators, and
  wherein each icon of the plurality of icons represents an identity from the subset of identities of the plurality of investigators.

4. The method of claim 1, comprising receiving, by the one or more processors, an approval indication for the clinical trial roster, and
  wherein the selectable record to reflect that the identities of investigators represented by the one or more selected icons have been added to the clinical trial roster is updated in response to receiving the approval indication.

5. The method of claim 1, wherein the user input indicating a subset of attributes comprises the user designation, and the user designation indicates to represent the first attribute by the first dimension of the multi-dimensional chart and the second attribute by the second dimension of the multi-dimensional chart.

6. The method of claim 1, wherein the subset of attributes includes the third attribute, and
  wherein the user input indicating a subset of attributes comprises the user designation, and the user designation indicates to represent the first attribute by the first dimension of the multi-dimensional chart, the second attribute by the second dimension of the multi-dimensional chart, and the third attribute by a size of each icon of the multi-dimensional chart.

7. The method of claim 1, wherein the data representing the set of attributes associated with each of the plurality of investigators comprises raw data and performance indicator scores.

8. The method of claim 1, wherein a color of each icon represents a fourth attribute of the represented investigator.

9. The method of claim 1, comprising altering, by the one or more processors, icons associated with the identities of investigators that have been added to the clinical trial roster.

10. The method of claim 1, comprising providing, by the one or more processors and for display on the computing device, a list of attributes associated with an identity of an investigator when a user selection device hovers over an icon that represents the identity of the investigator.

11. A system comprising:
obtaining, by one or more processors of a server system and from a selectable record in an aggregate database of the server system, identities of a plurality of investigators and data representing a set of attributes associated with each of the plurality of investigators from a first data set and a second data set, wherein:
  the first data set containing proprietary data associated with at least one of the investigators and received from a first set of databases,
  the second data set containing third-party data associated with at least one of the investigators and received from a second set of databases that is different from the first set of databases, and the selectable record enables the one or more processors to perform one or more adjustments to data of the identities of the plurality of investigators included within the aggregate database in a first time period that is shorter than a second time period for performing the one or more adjustments on data of the identities of the plurality of investigators included within the first set of databases and the second set of databases but not stored within the aggregate database;

receiving, by the one or more processors and from a computing device, a user input indicating a subset of attributes from the set of attributes associated with each of the plurality of investigators;

generating, by the one or more processors, a multi-dimensional chart that organizes the identities of the plurality of investigators based on the subset of attributes and a user designation of selected dimensions to reflect two or more of attributes from the subset of attributes, the multi-dimensional chart comprising:
a first dimension representing a first attribute from the subset of attributes;
a second dimension representing a second attribute from the subset of attributes; and
a plurality of icons,
each icon representing an identity of one of the plurality of investigators,
wherein each icon is positioned on the multi-dimensional chart along the first dimension according to a value of the first attribute associated with the represented identity and along the second dimension according to a value of the second attribute of the represented identity, and
wherein a graphical property of each icon represents a value of a third attribute of the represented identity;

linking, by the one or more processors, each icon included in the plurality of icons to the selectable record in the aggregate database so that user interactions with icons included in the plurality of icons by the computing device cause one or more attributes associated with the icons included in the plurality of icons to be altered within the aggregate database;

providing, by the one or more processors and for display on the computing device, a graphical user interface (GUI) including the multi-dimensional chart and a clinical trial roster;

receiving, by the one or more processors and from the computing device, a user selection of one or more icons from among the plurality of icons for inclusion in a clinical trial;

in response to receiving the user selection:
adding, by the one or more processors, identities of investigators represented by the one or more selected icons to the clinical trial roster;
updating, by the one or more processors, the selectable record to reflect that the identities of investigators represented by the one or more selected icons have been added to the clinical trial roster; and
updating, by the one or more processors and based on linking each icon included in the plurality of icons to the selectable record in the aggregate database, one or more attributes in the selectable record that are associated with the one or more selected icons.

12. The system of claim 11, comprising instructions which cause the one or more processors to perform operations comprising:
in response to adding the identities of investigators represented by the one or more selected icons to the clinical trial roster, modifying, by the one or more processors, an attribute associated with at least one of the added identities; and
causing, by the one or more processors, a linked icon in another multi-dimensional chart to be modified based on the attribute associated with the at least one of the added identities being modified.

13. The system of claim 11, comprising instructions which cause the one or more processors to perform operations comprising:
selecting, by the one or more processors and based on user selected filtering criteria, a subset of identities of the plurality of investigators, and
wherein generating the multi-dimensional chart comprises generating the multi-dimensional chart to organize the identities in the subset of identities of the plurality of investigators, and
wherein each icon of the plurality of icons represents an identity from the subset of identities of the plurality of investigators.

14. The system of claim 11, comprising instructions which cause the one or more processors to perform operations comprising:
receiving, by the one or more processors, an approval indication for the clinical trial roster, and
wherein the selectable record to reflect that the identities of investigators represented by the one or more selected icons have been added to the clinical trial roster is updated in response to receiving the approval indication.

15. The system of claim 11, wherein the user input indicating a subset of attributes comprises the user designation, and the user designation indicates to represent the first attribute by the first dimension of the multi-dimensional chart and the second attribute by the second dimension of the multi-dimensional chart.

16. A non-transient computer readable medium storing instructions that, when executed by one or more processors, cause the one or more processors to perform operations comprising:
obtaining, by the one or more processors of a server system and from a selectable record in an aggregate database of the server system, identities of a plurality of investigators and data representing a set of attributes associated with each of the plurality of investigators from a first data set and a second data set, wherein:
the first data set containing proprietary data associated with at least one of the investigators and received from a first set of databases,
the second data set containing third-party data associated with at least one of the investigators and received from a second set of databases that is different from the first set of databases, and
the selectable record enables the one or more processors to perform one or more adjustments to data of the identities of the plurality of investigators included within the aggregate database in a first time period that is shorter than a second time period for performing the one or more adjustments on data of the identities of the plurality of investigators included within the first set of databases and the second set of databases but not stored within the aggregate database;

receiving, by the one or more processors and from a computing device, a user input indicating a subset of attributes from the set of attributes associated with each of the plurality of investigators;

generating, by the one or more processors, a multi-dimensional chart that organizes the identities of the plurality of investigators based on the subset of attributes and a user designation of selected dimensions to reflect two or more of attributes from the subset of attributes, the multi-dimensional chart comprising:
a first dimension representing a first attribute from the subset of attributes;
a second dimension representing a second attribute from the subset of attributes; and
a plurality of icons,
each icon representing an identity of one of the plurality of investigators,
wherein each icon is positioned on the multi-dimensional chart along the first dimension according to a value of the first attribute associated with the represented identity and along the second dimension according to a value of the second attribute of the represented identity, and
wherein a graphical property of each icon represents a value of a third attribute of the represented identity;

linking, by the one or more processors, each icon included in the plurality of icons to the selectable record in the aggregate database so that user interactions with icons included in the plurality of icons by the computing device cause one or more attributes associated with the icons included in the plurality of icons to be altered within the aggregate database;

providing, by the one or more processors and for display on the computing device, a graphical user interface (GUI) including the multi-dimensional chart and a clinical trial roster;

receiving, by the one or more processors and from the computing device, a user selection of one or more icons from among the plurality of icons for inclusion in a clinical trial;

in response to receiving the user selection:
adding, by the one or more processors, identities of investigators represented by the one or more selected icons to the clinical trial roster;
updating, by the one or more processors, the selectable record to reflect that the identities of investigators represented by the one or more selected icons have been added to the clinical trial roster; and
updating, by the one or more processors and based on linking each icon included in the plurality of icons to the selectable record in the aggregate database, one or more attributes in the selectable record that are associated with the one or more selected icons.

17. The medium of claim 16, comprising:

in response to adding the identities of investigators represented by the one or more selected icons to the clinical trial roster, modifying, by the one or more processors, an attribute associated with at least one of the added identities; and causing, by the one or more processors, a linked icon in another multi-dimensional chart to be modified based on the attribute associated with the at least one of the added identities being modified.

18. The medium of claim 16, comprising selecting, by the one or more processors and based on user selected filtering criteria, a subset of identities of the plurality of investigators, and wherein generating the multi-dimensional chart comprises generating the multi-dimensional chart to organize the identities in the subset of identities of the plurality of investigators, and wherein each icon of the plurality of icons represents an identity from the subset of identities of the plurality of investigators.

19. The medium of claim 16, comprising receiving, by the one or more processors, an approval indication for the clinical trial roster, and wherein the selectable record to reflect that the identities of investigators represented by the one or more selected icons have been added to the clinical trial roster is updated in response to receiving the approval indication.

20. The method of claim 1, wherein the user input indicating a subset of attributes comprises the user designation, and the user designation indicates to represent the first attribute by the first dimension of the multi-dimensional chart and the second attribute by the second dimension of the multi-dimensional chart.

* * * * *